US008124831B2

(12) United States Patent
Caron et al.

(10) Patent No.: US 8,124,831 B2
(45) Date of Patent: Feb. 28, 2012

(54) TRANSGENIC MICE CARRYING FUNCTIONAL SINGLE NUCLEOTIDE POLYMORPHISMS IN BRAIN-SPECIFIC TRYPTOPHAN HYDROXYLASE

(75) Inventors: Marc G. Caron, Hillsborough, NC (US); Xiaodong Zhang, Durham, NC (US); Martin Beaulieu, Durham, NC (US); Raul R. Gainetdinov, Chapel Hill, NC (US); Tatyana D. Sotnikova, Chapel Hill, NC (US)

(73) Assignee: Duke University, Durham, NC (US)

( * ) Notice: Subject to any disclaimer, the term of this patent is extended or adjusted under 35 U.S.C. 154(b) by 421 days.

(21) Appl. No.: 11/825,202

(22) Filed: Jul. 5, 2007

(65) Prior Publication Data

US 2008/0010692 A1    Jan. 10, 2008

Related U.S. Application Data

(60) Provisional application No. 60/818,933, filed on Jul. 6, 2006.

(51) Int. Cl.
*A01K 67/027* (2006.01)
*G01N 33/00* (2006.01)

(52) U.S. Cl. ............................................. 800/18; 800/3
(58) Field of Classification Search .................... 800/18, 800/3
See application file for complete search history.

(56) References Cited

U.S. PATENT DOCUMENTS

| | | | |
|---|---|---|---|
| 4,736,866 | A | 4/1988 | Leder et al. |
| 4,873,316 | A | 10/1989 | Meade et al. |
| 5,589,604 | A | 12/1996 | Drohan et al. |
| 5,602,306 | A | 2/1997 | Townes et al. |
| 5,639,457 | A | 6/1997 | Brem et al. |
| 5,639,940 | A | 6/1997 | Garner et al. |
| 5,866,756 | A | 2/1999 | Giros et al. |
| 5,880,327 | A | 3/1999 | Lubon et al. |
| 5,958,429 | A | 9/1999 | Wong |
| 5,959,171 | A | 9/1999 | Hyttinen et al. |
| 6,166,288 | A | 12/2000 | Diamond et al. |
| 6,204,431 | B1 | 3/2001 | Prieto et al. |
| 6,218,595 | B1 | 4/2001 | Giros et al. |
| 6,252,132 | B1 | 6/2001 | Changeux et al. |
| 6,255,554 | B1 | 7/2001 | Lubon et al. |
| 6,331,658 | B1 | 12/2001 | Cooper et al. |
| 6,339,183 | B1 | 1/2002 | Sun |
| 6,344,596 | B1 | 2/2002 | Velander et al. |
| 6,465,714 | B2 | 10/2002 | Luthman et al. |
| 6,984,771 | B2 | 1/2006 | Roberds et al. |
| 7,022,893 | B1 | 4/2006 | Takeda et al. |
| 7,057,086 | B2 | 6/2006 | Vaughan et al. |
| 7,202,393 | B2 | 4/2007 | Matsushima |
| 2005/0039223 | A1 | 2/2005 | Steinlein et al. |
| 2005/0186137 | A1 | 8/2005 | Hen et al. |
| 2006/0029951 | A1 | 2/2006 | Caron et al. |
| 2006/0142375 | A1 | 6/2006 | Krishnan et al. |

FOREIGN PATENT DOCUMENTS

| | | |
|---|---|---|
| WO | WO 2004-007704 A2 | 1/2004 |
| WO | WO 2005-112906 A2 | 12/2005 |

OTHER PUBLICATIONS

Denning et al., New frontiers in gene targeting and cloning: success, application and challenges in domestic animals and human embryonic stem cells. Reproduction, 126(1): 1-11, 2003.*
Smith, Gene transfer in higher animals: theoretical considerations and key concepts, J Biotechnol. 99(1): 1-22, 2002.*
Matthaei, Genetically manipulated mice: a powerful tool with unsuspected caveats. J Physiol. 582(Pt 2):481-8, 2007.*
Capecchi, Targeted gene replacement, Scientific American, vol. 270, pp. 52-59, 1994.*
Gainetdinov et al., Role of serotonin in the paradoxical calming effect of psychostimulants on hyperactivity, Science 283(5400):397-401, 1999.*
Holmes et al., Evaluation of antidepressant-related behavioral responses in mice lacking the serotonin transporter, Neuropsychopharmacology, 27(6):914-23, 2002.*
Lira A at al. Altered Depression-Related Behaviors and Functional Changes in the Dorsal Raphe Nucleus of Serotonin Transporter-Deficient Mice. Biol Psychiatry (2003) vol. 54, pp. 960-971.
Sotnikova T D et al. Dopamine-Independent Locomotor Actions of Amphetamines in a Novel Acute Mouse Model of Parkinson Disease. PloS Biology (Aug. 2005) vol. 3, Issue 8, e271, pp. 1488-1500.
Bonasera et al. Mouse models of serotonin receptor function: toward a genetic dissection of serotonin systems. Pharmacol Ther 88 133-142 (2000).
Veenstra-Vanderweele et al. Pharmacogenetics and the serotonin system: initial studies and future directions. Eur J Pharmacol 410 165-181 (2000).
Gingrich et al. Dissecting the role of the serotonin system in neurophychiatric disorders using knockout mice. Psychopharmacology 155 1-10 (2001).
Walther D J et al. Synthesis of serotonin by a second tryptophan hydroxylase isoform. Science (Jan. 3, 2003), vol. 299, p. 76, and *Supporting Online Material*, pp. 1-7.
Walther et al. A unique central tryptophan hydroxylase isoform. Biochem Pharmacol 66 1673-1680 (2003).
Côte F et al. Disruption of the nonneuronal *tph1* gene demonstrates the importance of peripheral serotonin in cardiac function. PNAS USA (Nov. 13, 2003), vol. 100, No. 23, pp. 13525-13530.

(Continued)

*Primary Examiner* — Wu-Cheng Winston Shen
(74) *Attorney, Agent, or Firm* — Myers Bigel Sibley & Sajovec, P.A.

(57) ABSTRACT

Recombinant or transgenic non-human mammals are described having a mutant tryptophan hydroxylase 2 (Tph2) gene resulting in altered synthesis of 5-hydroxytryptophan and serotonin in the brain. In some embodiments the mutant tryptophan hydroxylase 2 gene contains mouse R439H and/or P447R functional mutations, or their corresponding mutations in other species. Congenic non-human mammals having mutant tryptophan hydroxylase 2 genes are also provided. Methods of screening a compound for serotonergic activity or activity in treating a serotonergic neurotransmission dysregulation disorder are provided, which include administering a test compound to a recombinant non-human mammal and then detecting the presence or absence of serotonergic activity, or activity in treating a serotonergic neurotransmission dysregulation disorder, in the mammal. A cell such as a nerve cell (e.g., a central nervous system neuron) isolated from a transgenic or congenic mammal is also disclosed, along with cell cultures containing these cells.

44 Claims, 7 Drawing Sheets

OTHER PUBLICATIONS

De Luca et al. Analysis of the novel TPH2 gene in bipolar disorder and suicidality. Molecular Psychiatry (2004), vol. 9, pp. 896-897.

Garriock Ha et al. Lack of association of TPH2 exon XI polymorphisms with major depression and treatment resistance. Molecular Psychiatry 10:976-977. Jul. 12, 2005.

Correspondence from Blakely; Zhou et al; Bogaert et al; Glatt et al. and Zhang et al. Neuron 48:701-706. Dec. 8, 2005.

Delorme R et al. No human tryptophan hydroxylase-2 gene R441H mutation in a large cohort of psychiatric patients and control subjects. Biological Psychiatry 60:202-203. 2006.

Sheehan K et al. No association between TPH2 gene polymorphisms and ADHD in a UK sample. Neuroscience Letters 412(2)105-107. Jan. 29, 2007.

Sacco R et al. Case-control and family-based association studies of candidate genes in autistic disorder and its endophenotypes: TPH2 and GLO1. BMD Medical Genetics 8(11):1471-1480. Mar. 8, 2007.

Beaulieu J-M et al. Role of GSK3β in behavioral abnormalities induced by serotonin deficiency. PNAS (Jan. 29, 2008), vol. 105, No. 4, pp. 1333-1338.

Fulmer T. The great (mouse) depression. Science-Business eXchange (Feb. 7, 2008), vol. 1, No. 2, pp. 1, 10-11.

International Search Report and Written Opinion, PCT/US05/17952, mailed Mar. 18, 2008.

McKinney J et al. A loss-of-function mutation in tryptophan hydroxylase 2 segregating with attention-deficit/hyperactivity disorder. Molecular Psychiatry (2008), vol. 13, pp. 365-367.

Cervo L, et al. Genotype-dependent activity of tryptophan hydroxylase-2 determines the response to citalopram in a mouse model of depression. The Journal of Neuroscience (Sep. 7, 2005) 25(36):8165-8172.

Cook M, et al. Anxiety in the elevated zero-maze is augmented in mice after repeated daily exposure. Behavior Genetics (2002) 32(2):113-118.

Crawley J N, et al. Behavioral phenotypes of inbred mouse strains: implications and recommendations for molecular studies. Psychopharmacology (1997) 132:107-124.

Crowley J J, et al. Strain-dependent antidepressant-like effects of citalopram in the mouse tail suspension test. Psychopharmacology (2005) 183:257-264.

Holmes A, et al. Reduced aggression in mice lacking the serotonin transporter (2002) 161:160-167.

Kulikov A, et al. Association between Tph2 gene polymorphism, brain tryptophan hydroxylase activity and aggressiveness in mouse strains. Genes, Brain and Behavior (2005) 4:482-485.

Lira A, et al. Altered depression-related behaviors and functional changes in the dorsal raphe nucleus of serotonin transporter-deficient mice. Biol. Psychiatry (2003) 54:960-971 (Abstract only).

Lucki I, et al. Sensitivity to the effects of pharmacologically selective antidepressants in different strains of mice. Psychopharmacology (2001) 155:315-322.

Sankoorikal G, et al. A mouse model system for genetic analysis of sociability: C57BL/6J Versus BALB/cJ inbred mouse strains (2006) 59:415-423.

Winge I, et al. Characterization of wild-type and mutant forms of human tryptophan hydroxylase 2. Journal of Neurochemistry (2007) 100:1648-1657.

Zhang X, et al. Tryptophan hydroxylase-2 controls brain serotonin synthesis. Science (Jul. 9, 2004) 305:217.

Zhang X, et al. Loss-of-function mutation in tryptophan hydroxylase-2 identified in unipolar major depression. Neuron (Jan. 6, 2005) 45:11-16.

Zhang X, et al. Functional polymorphisms of the brain serotonin synthesizing enzyme tryptophan hydroxylase-2. Coll. Mol. Life Sci. (2006) 63:6-11.

Grohmann M et al. Alternative splicing and extensive RNA editing of human TPH2 transcripts. PLoS ONE. Jan. 2010; 5(1): e8956, 11 pp.

Siesser WB et al. Tryptophan hydroxylase 2 genotype determines brain serotonin synthesis but not tissue content in C57B1/6 and BALB/c congenic mice. Neurosci. Lett. (2010), doi:10.1016/j.neulet.2010.06/035.

Tenner et al., "The mTPH2 C1473G single nucleotide polymorphism is not responsible for behavioural differences between mouse strains," *Neuroscience Letters* 431:21-25 (2008).

Kulikov et al., "The C1473G polymorphism in gene tph2 is the main factor mediating the genetically defined variability of tryptophan hydroxylase-2 activity in the mouse brain," Genetika 43(12):1676-1681 (2007) (Abstract Only).

Calcagno et al., "Strain differences in basal and post-citalopram extracellular 5-HT in the mouse medial prefrontal cortex and dorsal hippocampus: relation with tryptophan hydroxylase-2 activity," *J. Neurochem.* 130:1111-1120 (2007).

Gutnecht et al., "Deficiency of brain 5-HT synthesis but serotonergic neuron formation in Tph2 knockout mice," *J. Neural Transm.* 115(8):1127-1132 (2008) (Abstract Only).

* cited by examiner

TRANSGENIC MICE CARRYING FUNCTIONAL SINGLE NUCLEOTIDE POLYMORPHISMS IN BRAIN-SPECIFIC TRYPTOPHAN HYDROXYLASE

RELATED APPLICATIONS

This application claims the benefit under 35 U.S.C. §119 (e) of U.S. Provisional Patent Application Ser. No. 60/818,933, filed Jul. 6, 2006, the disclosure of which is incorporated herein by reference in its entirety.

STATEMENT OF GOVERNMENT SUPPORT

This invention was made with Government support under grant no. MH-60451 from the National Institutes of Health. The United States Government has certain rights to this invention.

FIELD OF THE INVENTION

The present invention concerns the engineering of non-human mammals having a mutant tryptophan hydroxyase 2 (Tph2) gene and methods of making and using the same.

BACKGROUND OF THE INVENTION

Serotonin (5-hydroxytryptamine or 5-HT) is a monoaminergic neurotransmitter that has been implicated in embryonic development and in many physiological functions of the central nervous system, including sleep, appetite, aggression and sexual behavior. Serotonergic neurotransmission is involved in the etiology or treatment of many neuropsychiatric disorders, such as depression, schizophrenia, attention deficit hyperactivity disorder (ADHD), panic disorder, obsessive-compulsive disorder, social phobia, bipolar disorder, premenstrual syndrome or premenstrual dysphoric disorder (PMDD), bulimia nervosa and other eating disorders, autistic disorder, stroke, migraine, and nausea.

The serotonergic system is also the primary target for a number of drugs frequently used in psychiatry, such as tricyclic antidepressants, selective serotonin reuptake inhibitors (SSRIs), monoamine oxidase (MAO) inhibitors, anxiolytics (such as Buspirone), psychostimulants (such as cocaine), and hallucinogenic drugs (such as lysergic acid diethylamide (LSD) and (+)-3,4-methylenedioxyamphetamine (MDMA, "ecstasy")). For example, drugs that enhance serotonin neurotransmission are commonly used in the treatment of depression, anxiety and other mood disorders.

Recent investigations of naturally-occurring genetic polymorphisms in humans and other species have identified mutations in the gene of the brain isoform of tryptophan hydroxylase (Tph2), a rate-limiting enzyme necessary for serotonin production, that lead to pronounced reductions in enzyme activity and serotonin synthesis. This enzyme catalyzes the conversion of the amino acid tryptophan to 5-hydroxytryptophan (5HTP), and this step is followed by decarboxylation of 5HTP by the L-aromatic amino acid decarboxylase to produce 5HT (serotonin).

Mice having a C1473G single nucleotide polymorphism (SNP) in Tph2 corresponding to a P447R mutation in the encoded protein showed a marked reduction in 5HT content in brain tissues (Zhang et al., 2004, Science 305:217). The expression of this Tph2 variant in specific inbred mouse lines is associated with reduced brain 5HT synthesis (Zhang et al., 2004, Science 305:217) and differences in aggressive behavior (Kulikov et al., 2005, Genes, Brain and Behav. 4:482-485), pre-mRNA editing of the 5HT2C receptor (Englander et al., 2005, J. Neurosci. 25:648-651), as well as responsiveness to SSRIs (Cervo et al., 2005, J. Neurosci. 25:8165-8172; Crowley et al., 2005, Psychopharmacol. (Berl.) 183:257-264). However, these studies compared different strains of inbred mice, and the potential contribution of other genetic variations in these mice cannot be ruled out.

A rare R441H Tph2 functional variant has also been identified in a small cohort of elderly patients with major unipolar depression (Zhang et al., 2005, Neuron 45:11-16). The R441H Tph2 mutations results in a reduction of hydroxylase activity by about 80% when expressed in a cell culture system. Large-scale genetic analyses have associated several non-coding polymorphisms in the human Tph2 gene with depression, bipolar disorder and suicidality (Harvey et al., 2004, Mol. Psychiatry 9:980-981; Zill et al., 2004, Mol. Psychiatry 9:1030-1036; Harvey et al., 2007, Psychiatr. Genet. 17:17-22; de Lara et al., 2007, Biol. Psychiatry 62:72-80; Lopez et al., 2007, Bio. Psychiatry 61:181-186). Naturally occurring functional polymorphisms in the Tph2 gene have also been identified in mice (Zhang et al., 2004, Science 305:217), rhesus monkeys (Chen et al., 2006, Mol. Psychiatry 11:914-928) and chimpanzees (Hong et al., 2007, Neurosci. Lett. 412:195-200).

Phenylalanine hydroxylase (PAH), an enzyme that is related to Tph2, also has a multiplicity of variants that lead to the development of human pathologies. For example, the PAH gene has 307 missense mutations have been reported to cause various degrees of phenylketonuria (Zhang et al., Cell Mol. Life Sci., 2006, 63: 6-11; Pey et al., 2003, 21: 370-378). This suggests that multiple functional Tph2 mutations may also exist in humans and potentially play a role in the etiology of mood disorders (See, e.g., U.S. Patent Application Publication No. 2006/0029951).

SUMMARY OF THE INVENTION

A first aspect of the present invention is a recombinant or transgenic non-human mammal (e.g., a mouse) having a mutant tryptophan hydroxylase 2 (Tph2) transgene, wherein the mutant tryptophan hydroxylase 2 transgene results in altered synthesis of 5-hydroxytryptophan and serotonin in the brain of said mammal. In some embodiments the mammal is a knock-in gene mutated mammal. The mutant tryptophan hydroxylase 2 transgene can, in some embodiments, contain a mutation selected from the group consisting of mR439H and mP447R, and their corresponding mutations in other species. Mammals of the invention may be infant, adolescent or adult, may be first generation or progeny, and may be homozygotes or heterozygotes for the mutant tryptophan hydroxylase 2 gene.

Another aspect is a congenic non-human mammal having a mutant Tph2 gene, wherein the mutant Tph2 gene results in altered synthesis of 5-hydroxytryptophan and serotonin in the brain of said mammal. The mutant tryptophan hydroxylase 2 gene can, in some embodiments, contain a mutation selected from the group consisting of mR439H and mP447R, and their corresponding mutations in other species. Mammals of the invention may be infant, adolescent or adult, may be first generation or progeny, and may be homozygotes or heterozygotes for the mutant tryptophan hydroxylase 2 gene.

A further aspect of the invention is a method of screening a compound for serotonergic activity or activity in treating a serotonergic neurotransmission dysregulation disorder, comprising: administering a test compound to a recombinant non-human mammal as described herein; and then detecting the presence or absence of serotonergic activity, or activity in treating a serotonergic neurotransmission dysregulation disorder, in said mammal.

A further aspect of the invention is a cell such as a nerve cell (e.g., a central nervous system neuron) isolated from a mammal as described herein, along with cell cultures comprising, consisting of or consisting essentially of such cells (that is, produced by culturing such cells). Such cells and cell cultures are useful in vitro for screening the activity of candidate compounds for their effect on serotonergic neurotransmission, and for their activity in treating serotonergic neurotransmission dysregulation disorders.

The present invention is explained in greater detail in the drawings herein and the specification set forth below.

DETAILED DESCRIPTION OF THE PREFERRED EMBODIMENTS

Figure 1:
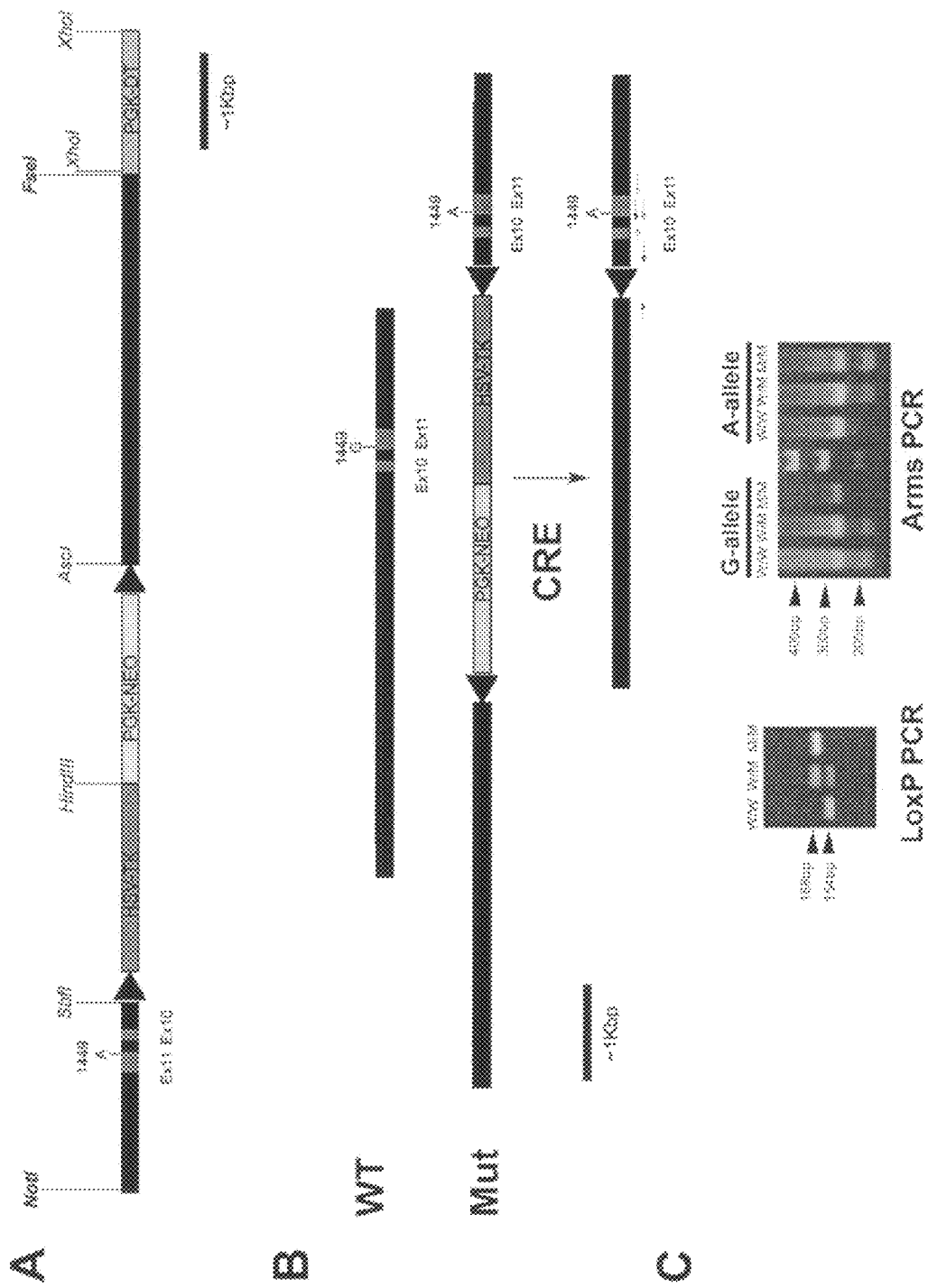
FIG. 1. Generation of mR439H Tph2 knock-in mice. A: Targeting construct containing the mutant mTph2 allele. Arrowheads correspond to LoxP elements, Ex: exon. B: Recombination events in the mTph2 locus. PCR primers (small arrows): primers used to detect the residual LoxP element following CRE mediated recombination; ARMS-PCR outer primers; ARMS-PCR allele specific primers. C: PCR amplifications from mouse tail DNA showing the presence of a residual LoxP element and of the G1449A mutation in heterozygote (W/M) and homozygote (M/M) Tph2 knockin mice. W: wild-type G-allele. M: mutant A-allele.

We have found that mice carrying mutant Tph2 alleles can be used as a model to study the impact of serotonergic neurotransmission disregulation. Knock-in mice were generated with a Tph2 mR439H mutation that is equivalent to a rare human variant of Tph2 (R441H) identified in a small cohort of patients with unipolar major depression (Zhang et al., 2005, Neuron 45:11-16). We have found that genetically modified mice carrying two copies of the equivalent R439H functional polymorphisms in the mouse Tph2 gene (mTph2) display more than 80% reduction of brain 5-HT synthesis, while inbred mice carrying the P447R mutant display a 40% reduction of brain 5-HT synthesis, each indicating a sever loss in function of this important rate-limiting enzyme.

These functional Tph2 mutations in mice result in marked reduction of 5-HT synthesis and tissue content, as well as abnormalities in tests used to model depression-related behaviors. The Tph2 mutations engineered in these mice are therefore sufficient to disrupt brain 5-HT synthesis and induce behavioral abnormalities. Animals such as these provide a unique model to study the impact of 5-HT synthesis on brain functions and provide a model system for future drug development.

The disclosures of all cited United States Patent references are hereby incorporated by reference to the extent they are consistent with the disclosure herein. As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" and "/" refer to and encompass any and all possible combinations of one or more of the associated listed items, as well as the lack of combinations when interpreted in the alternative ("or").

A "recombinant" or "transgenic" non-human mammal as used herein refers to a non-human mammal that has a genome or genetic material that is augmented or altered in some fashion with a construct comprising a recombinant nucleic acid (i.e., a "transgene") that is introduced into one or more of the somatic and germ cells of the mammal. The nucleic acid may be of the same species (homologous) or of another species (heterologous) with respect to the host mammal. Preferably, the transgene is a mutant Tph2 gene or a portion thereof. The nucleic acid may be present in cells as an extrachromosomal element or may be stably integrated into the genome of some, most or all cells of the host animal. "Chimeric" mammals are animals in which a portion of their cells are augmented or altered with the transgene, and a portion of their cells are not augmented or altered with that transgene.

A "recombinant" nucleic acid refers to a nucleic acid that has been manipulated in vitro. In some embodiments the nucleic acid may include selection marker coding regions, e.g., a thymidine kinase/neomicine selection marker region. In some embodiments these selection marker regions are removed in subsequent steps according to known techniques. For example, the selection marker may be "floxed," i.e., flanked by loxP sites that are recognized by Cre recombinase, which allows context-specific excision of the nucleic acid segment situated between the loxP sites.

"Congenic" or "recombinant congenic" strains may be created, which are useful to create non-human mammals (e.g., mice) that are nearly identical except for a selected genotype/phenotype (see, e.g., U.S. Pat. No. 7,202,393 to Matsushima). Congenic animals can be generated by mating two genetically distinct inbred strains and then backcrossing the descendants with one of the parental or ancestral strains (the "recipient" strain), e.g., for two generations, followed by inbreeding sister and brother, with or without selecting for particular markers or phenotypes. Using this method, the recipient on average contributes the greater proportion of the genome to each congenic strain. Backcrossing generally increases homozygosity twice as fast as sibling mating. Other methods of creating congenic strains may also be used, and alternative methods may be used, as will be appreciated by those of skill in the art. For example, the number of backcrosses may vary, resulting in different genomic proportions from the recipient. Selection for the genotype/phenotype of interest may also be performed at certain steps as desired.

"Serotonergic neurotransmission dysregulation disorder" as used herein refers to any disorder in which an increase or decrease in available serotonin contributes, at least in part, to a disease, disorder, or condition. Examples of serotonergic neurotransmission dysregulation disorders include, but are not limited to, depressive disorder, anxiety disorder, social anxiety disorder, generalized anxiety disorder, bipolar disorder, schizophrenia, autism, epilepsy, mood disorders, alcohol or substance abuse and associated disorders, panic disorder, migraine, obesity, bulimia, anorexia, premenstrual syndrome, menopause, sleep disorders, attention-deficit/hyperactivity disorder (ADHD), Tourette syndrome, aggression, obsessive compulsive disorder, pathological gambling, novelty seeking, borderline personality disorders, antisocial personality disorder, suicidility, eating disorders, sexual dysfunction, dementia, social phobia, fibromyalgia, overactive bladder, chronic fatigue syndrome, chronic pain, sudden infant death syndrome, post-traumatic stress syndrome, and Alzheimer's disease. These terms have their usual meaning in the art. See, e.g., DSM-IV; see also U.S. Patent Application Publication No. 2006/0029951 to Caron et al., which is incorporated by reference herein in its entirety.

By "available" serotonin or "availability" of serotonin it is meant the amount of 5-HT that is available to stimulate a receptor at the synapse or present in the extracellular space. Serotonin availability can be modulated, e.g., by changing the synthesis, reuptake or degradation of 5-HT. In neurons, serotonin is synthesized in a two-step enzymatic reaction. The first rate-limiting step involves the hydroxylation of tryptophan into 5-Hydroxytryptophan (5-HTP) by a tryptophan dehydroxylase. The second step involves the decarboxylation of 5-HTP into 5-HT. Following its synthesis, 5-HT is stored into synaptic vesicles and is available for release. Following its release and the stimulation of 5-HT receptors, 5-HT is either degraded or reuptaken and stored in synaptic vesicles. Serotonergic neurotransmission is thought to be terminated primarily by its reuptake into cells.

"Wild type" gene sequences of a given species are those DNA or protein sequences that are most highly conserved within or across species (e.g., the proline at position 447 of mouse Tph2). The gene for Tph2 is known and described at GenBank accession numbers NM_173353 (human); NM_173391 (mouse); and NM_173839 (rat). See also M. Bader and D. Walther, PCT Patent Application WO 2004/007704. These genes are referred to as the "wild type" (i.e., non-mutant) Tph2 genes herein, subject to the proviso that "wild type" when referring to mouse refers to a nucleic acid encoding a proline at position 447 of the encoded protein. Note that Walther et al. submitted the mutant (P447R) for mouse at GenBank (NM_173391) and likewise in WO 2004/007704. We have found and described the wild type version in mice (P447), which is otherwise identical to the version previously defined in GenBank and WO 2004/007704 (See, e.g., U.S. Patent Application Publication No. 2006/0029951 to Caron et al.).

Accordingly, a "wild type" mouse or other non-human mammal is one that does not contain a mutant Tph2 gene or a mutant Tph2 transgene. In preferred embodiments, the genome or genetic material of the wild type mammal is otherwise significantly or substantially identical to the transgenic, recombinant and/or congenic non-human mammal having a mutant Tph2 gene (e.g., littermates). Animals of the present invention are, in general, mammals, including primates, such as monkeys, more preferably rodents, and are more particularly mice and rats. Animals may be male or female, and may be of any age including adult.

The mutant Tph2 gene differs in DNA sequence from the corresponding wild type Tph2, as defined above, but still shares at least 75, 80, 85, 90, 95, or 99% or more sequence identity with the wild type Tph2 gene of the same species, as defined. A "mutant" Tph2 gene is one that differs in DNA sequence at one or more bases from the wild type Tph2 gene. The mutations may or may not result in a functional alteration of the expressed mutant Tph2 gene. Tryptophan hydroxylase is considered to be the rate-limiting enzyme in serotonin synthesis. Tryptophan hydroxylase 2 (Tph2) is preferentially expressed in brain tissues.

A "functional" mutation in the Tph2 gene is a mutation that results in a change in activity levels of the Tph2 gene as compared to the corresponding wild type Tph2 gene. For example, the mutation may be a single nucleotide polymorphism (SNP) in the gene sequence that results in a change in the encoded protein (e.g., a P447R mutation). The encoded protein thus has a different amino acid sequence, but still has at least 70, 75, 80, 85, 90, 95, or 99% or more homology with the corresponding wild type protein. This change in encoded amino acid sequence in a "functional" mutation results in a change in activity levels (i.e., increase or decrease) in the Tph2 enzyme functionality, such that levels of 5-HTP and/or 5-HT "present" or "available" in brain tissues, and/or Tph2 "synthesis rate," is increased or decreased by at least 25, 40, 50, 60, 70, 80, or 90% or more as compared to the wild type Tph2. This Tph2 functionality can be measured by methods known in the art. For example, monitoring the accumulation of the 5-HT precursor and Tph2 product, 5-HTP, following treatment of mice with the aromatic amino acid decarboxylase inhibitor, m-hydroxybenzylhydrazine, provides a direct assessment of Tph2 activity in vivo (see Zhang et al., 2004, Science 305:217).

A "knock-in" of a target gene generally refers to the replacement of endogenous genetic material (e.g., a gene or a portion of a gene) with exogenous genetic material (i.e., a recombinant nucleic acid). The term "knock-in" as used herein also includes alterations of genetic material by introduction of one or more additional copies of the recombinant nucleic acid, with or without replacing the endogenous gene. The term "knock-in" is intended to include first generation mice as well as progeny thereof that have the transgene in at least one allele thereof.

In an alternative approach, a transgenic non-human mammal may be created in which one or more of the endogenous genes encoding and expressing Tph2 as described herein is "knocked-out" or otherwise substantially inactivated. This may be accomplished according to known procedures, e.g., by deleting all or a portion of the Tph2 gene itself, deleting regulatory elements necessary for Tph2 expression, or otherwise altering the expression/translation of the endogenous Tph2 gene.

By the term "express" or "expression" of a nucleic acid coding sequence, it is meant that the sequence is transcribed, and optionally, translated. Typically, according to the present invention, expression of a coding region will result in production of the encoded protein or polypeptide.

The production of recombinant animals (e.g., "knock-in" and "knock-out") is known and can be carried out in accordance with known techniques or variations thereof which will be apparent to those skilled in the art, for example as disclosed in: U.S. Pat. No. 7,022,893 to Takeda et al. and U.S. Pat. No. 6,218,595 to Giros et al., as well as U.S. Pat. No. 6,344,596 to W. Velander et al. (American Red Cross); U.S. Pat. No. 6,339,183 to T. T. Sun (New York University); U.S. Pat. No. 6,331,658 to D. Cooper and E. Koren; U.S. Pat. No. 6,255,554 to H. Lubon et al. (American National Red Cross; Virginia Polytechnic Institute); U.S. Pat. No. 6,204,431 to P. Prieto et al. (Abbott Laboratories); U.S. Pat. No. 6,166,288 to L. Diamond et al. (Nextran Inc., Princeton, N.J.); U.S. Pat. No. 5,959,171 to J. M. Hyttinin et al. (Pharming BV); U.S. Pat. No. 5,880,327 to H. Lubon et al. (American Red Cross); U.S. Pat. No. 5,639,457 to G. Brem; U.S. Pat. No. 5,639,940 to I. Garner et al. (Pharmaceutical Proteins Ltd.; Zymogenetics Inc); U.S. Pat. No. 5,589,604 to W. Drohan et al. (American Red Cross); U.S. Pat. No. 5,602,306 to Townes et al. (UAB Research Foundation); U.S. Pat. No. 4,736,866 to Leder and Stewart (Harvard); and U.S. Pat. No. 4,873,316 to Meade and Lonberg (Biogen).

Tph2 mutations suitable for carrying out the present invention include, but are not limited to, those which result in a substitution mutation at the following positions of mouse Tryptophan hydroxylase 2, for example: A63, V64, F66, L75, F82, I92, R95, E103, P150, W151, P153, D160, L173, R189, E209, V221, P242, G249, R274, P275, V276, R283, R292, P306, Y308, E311, A331, I337, A340, S341, L342, A344, K351, V419, A426, A434, R439, Y444, P447, Y448, and Q466. Corresponding mutations in the corresponding locations of other species based upon alignment of the sequences are also useful in carrying out the present invention, even though the aligned position of the specific amino acid may differ. Examples are listed in Table 1 (see also U.S. Patent Application Publication No. 2006/0029951 to Caron et al.).

TABLE 1

Corresponding Tph2 mutations across species.

| human | mouse | rat | chicken | zebrafish | pufferfish |
|---|---|---|---|---|---|
| A65 | A63 | A60 | A64 | A35 | A61 |
| V66 | V64 | V61 | V65 | V36 | V62 |
| F68 | F66 | F63 | F67 | F38 | F64 |
| L77 | L75 | L72 | L76 | L47 | L73 |
| F84 | F82 | F79 | F83 | F54 | F80 |
| I94 | I92 | I89 | I93 | I64 | I90 |
| R97 | R95 | R92 | R96 | R67 | R93 |
| E105 | E103 | E100 | E104 | E75 | E101 |
| P152 | P150 | P147 | P151 | P135 | P148 |
| W153 | W151 | W148 | W152 | W136 | W149 |
| P155 | P153 | P150 | P154 | P138 | P151 |
| D162 | D160 | D157 | D161 | D145 | D158 |
| L175 | L173 | L170 | L174 | L158 | L171 |
| R191 | R189 | R186 | R190 | R174 | R187 |
| E211 | E209 | E206 | E210 | E194 | E207 |
| V223 | V221 | V218 | V222 | V206 | V219 |
| P244 | P242 | P239 | P243 | P227 | P240 |
| G251 | G249 | G246 | G250 | G234 | G247 |
| R276 | R274 | R271 | R275 | R259 | R272 |
| P277 | P275 | P272 | P276 | P260 | P273 |
| V278 | V276 | V273 | V277 | V261 | V274 |
| R285 | R283 | R280 | R284 | R268 | R281 |
| R294 | R292 | R289 | R293 | R277 | R290 |
| P308 | P306 | P303 | P307 | P291 | P304 |
| Y310 | Y308 | Y305 | Y309 | Y293 | Y306 |
| E313 | E311 | E308 | E312 | Y296 | E309 |
| A333 | A331 | A328 | A332 | A316 | A329 |
| I339 | I337 | I334 | I338 | I322 | I335 |
| A342 | A340 | A337 | A341 | A325 | A338 |
| S343 | S341 | S338 | S342 | S326 | S339 |
| L344 | L342 | L339 | L343 | L327 | L340 |
| A346 | A344 | A341 | A345 | A329 | A342 |
| K353 | K351 | K348 | K352 | K336 | K349 |
| V421 | V419 | V416 | V420 | V404 | V417 |
| E423 |  | E418 | E422 | E406 | E419 |
| A428 | A426 | A423 | A427 | A411 | A424 |
| A436 | A434 | A431 | A435 | A419 | A432 |
| R441 | R439 | R436 | R440 | R424 | R437 |
| Y446 | Y444 | Y441 | Y445 | Y429 | Y442 |
| P449 | P447 | P444 | P448 | P432 | P445 |
| Y450 | Y448 | Y445 | Y449 | Y433 | Y446 |
| Q468 | Q466 | Q463 | Q467 |  | Q464 |

Note that 43 mutations are identified, some identified by sequence analysis and some by sequence identity compared to PAH. Table 1 lists corresponding mutations in Tph2 in six different species, which corresponding mutations are also useful for carrying out the present invention. It is striking that all 43 amino acids for these mutations are virtually identical in Tph2 in six different species (except in two positions). This strongly indicates that mutations in similar position in Tph2 have a like functional impact on serotonin production in other species.

Progeny of first generation animals produced by the methods described herein are also an aspect of the present invention. Such animals, or congenic animals, of the invention can be produced in accordance with known techniques, including, but not limited to, those described in U.S. Pat. No. 6,465,714. In general, animals of the present invention are created by (a) providing a first (male or female) recombinant parent animal produced as described above, and a second parent animal, wherein at least the first parent exhibits the phenotype of the invention (e.g., decreased brain 5-HTP and 5-HT levels); and then (b) crossing the first and second parent mice with one another to produce a progeny mouse that exhibits that phenotype. Subsequent generations can be further produced in accordance with known techniques.

Animals of the invention are useful in like manner as serotonin or dopamine transporter knock-out mice such as described in A. Lira et al., 2003, Biol Pschyiatry 54:960-971 (2003), and B. Giros et al., U.S. Pat. No. 6,218,595. Among other things, mice of the invention are useful for screening candidate compounds for serotonergic activity, or activity in treating serotonergic neurotransmission dysregulation disorders attributed to reduced serotonergic activity, examples of which include but are not limited to depression, anxiety, schizophrenia, appetite disorders (e.g. bulimia nervosa, anorexia), addiction (tobacco, narcotic, drug, alcohol, etc.). Such compounds include compounds that affect serotonin availability, e.g., fluoxetine (a selective serotoning reuptake inhibitor (SSRI)).

Numerous screening tests of non-human mammals for behavioral phenotypes or abnormalities found in, or consistent with, human serotonergic neurotransmission dysregulation disorders are known. Examples include, but are not limited to, the tail suspension test (for antidepressant activity), the forced swim test (for antidepressant activity), learned helplessness (for depression), fear conditioning (for learning and emotional processing conditions), the resident intruder test (social interactions), the Morris water maze test, the radial maze test, operant conditioning tests (reward, learning), self-administration tests (reward learning, addiction), open field locomotion (psychostimulant responses, can also be used for addiction), place preference tests (for addiction), zero maze tests (for anxiety), latency to feeding (for anxiety), shock escape paradigms (for anxiety), and open field exploration tests (for anxiety). See Crawley et al., 1997, Psychopharmacology, 132:107-124; see also U.S. Pat. No. 6,984,771 to Roberds et al.

Assessment of "behavioral despair" is the most common approach used to assess actions of antidepressants in mice (Crowley et al., 2004, Pharmacol. Biochem. Behav. 78:269-274; Lucki et al., 2001, Psychomparmacology (Berl) 155: 315-322). For example, in the Porsolt forced-swim and the tail-suspension tests, drug-induced reductions in immobility times are predictive of antidepressant activities of drugs.

"Aggression" or aggressive behavior can be tested in mice using a model of spontaneous intermale aggression as described (Kulikov et al., 2005, Genes, Brain and Behav. 4:482-485). In this model, intermale aggression is measured in encounters between pairs of males using two indices: 1) the level of aggressiveness, using the percentage of mice attacking, and 2) intensity of the aggression, measured by the number of attacks. Comparisons can be made between wild-type, heterozygous and homozygous Tph2 mutant mice. Aggression is "altered" when there is either an increased or decreased amount or level of aggression as compared to a corresponding wild-type animal. Increased/decreased aggression may be shown by differences in either the level of aggressiveness or the intensity of the aggression according to various behavioral models or paradigms known in the art.

Impaired "social interactions" are common in many types of psychiatric disorders (e.g., autism, schizophrenia, etc.). Various behavioral tests are known in the art for altered social interactions, e.g., social choice paradigms (see Sankoorikal et al., 2005, Biol Psychiatry, 59:415-423).

The present invention is explained in greater detail in the following non-limiting Examples.

EXAMPLES

The results presented here provide direct in vivo evidence that a Tph2 genetic variation is sufficient to affect brain 5-HT synthesis and induce biochemical and behavioral changes associated with reduced 5-HT neurotransmission. The results show that a functional Tph2 gene mutation, which has been identified in patients suffering from depression, produces profound reductions of brain 5-HT synthesis in mice. Moreover, a single copy of this genetic variant is sufficient to significantly reduce brain 5-HT synthesis and induce behavioral abnormalities use to model mood disorders in rodents.

The R439H Tph2 knock-in mice represent a unique animal model to study the biological functions of Tph2 and brain 5-HT. Furthermore, because an equivalent R441H polymorphism has been identified in humans, observations made in these mice have direct clinical relevance to human psychiatric conditions.

Example 1

Generation of R439H Tph2 knock-in mice. "Knock-in" mice carrying the R439H mTph2 allele equivalent to the R441H hTPH2 allele identified in major unipolar depression patients (Zhang et al., 2005, Neuron 45:11-16) were produced as follows. A 4.6 kb "long arm" (SEQ ID: 1, See Table 2 below) and a 2.0 kb "short arm" (SEQ ID: 2, See Table 3 below) were cloned by PCR using EXL® DNA polymerase (Stratagene, La Jolla, Calif.) using genomic DNA obtained from 129S6/SvEv mice as a template. The long arm corresponded to sequences from mTph2 intron 9, while the short arm contained intron 9 sequences as well as exon 10, intron 10, exon 11, and about 1 kb of the 3'UTR of the mTph2 gene. To engineer the R439H, the guanine 1449 encoded in exon 11 was changed to an adenine using site directed mutagenesis. The long arm and short arm were then subcloned to a targeting vector, resulting in the insertion of a floxed herpes virus thymidine kinase/neomicine (TK/NEO) selection cassette in the ninth intron of the gene (FIG. 1A).

TABLE 2

LONG ARM Sequence (4657 bp)
(SEQ ID NO: 1)
TTTCCCTCAAAATCTAACCAGTCCTAATATAGAGAGTGAGGATAACAGGT

TTACATCTACAATAGTTGAGATCATACCTCTGTGTCCCTGTAGAAATGGG

TGTCTGAGAGGAAGGAAGATGTCAAGTGAGTCAGAGAAGCCACAATTGCA

GTTTGAGTCTTACAAGTCTCATACCCGGGACCATTCTTTCCCTATAGTTC

TAGACCTCGGGGGCGAGGGAGGACATGCTTATTAGGCAGCACATACAAT

CCTCTCTGGACTGAATTAGGGATGGTAACTAAATATGTTAAGCACGTCCC

ATGATAGCCATTTGCATGCATTTCCCGTTTAATTCTGACCACAACCTTGG

GCTATCGAGTCCATTAGGTTCCCCAAACTGTACAGGAAGGAACAGAGCCA

AATTTAACCTCCAAGATTGAGATGTAGGCTCTGAATTATCTTGTATTATT

ATTCCAGCAACTGGAAAATTTTGATGTCAAAAGGATAGTGACCAATACCA

AGTAACTGGTACTTGGTGGTCAAGGGTGACATGGGTTACCTCAGGACCAA

TAGGAAAGGCAGCATTGGTAAATTGACACAGGCAAAGTGGAGAGTGCTCT

GGGTTTATAGGTCTTGTTAAAATTATACTGCAAGAAGATTCTTAGATTCA

TGCAGGCCAGAGTATTTTAGATTTACCACAGAGGAAACTGCAGCTCATTT

TGAGATACTTCCTCATCTGGTATTACACTGTTACTGGGTTAAAAATTTCT

CTTCAGTTCTTGTGTTCTTGAAGGAAAGAATTCAGTTGAGAAACAGTTAG

ATCAAGTAGAAGTTTATTTAGCAAAGAAGTGTAGATACTCCAAAGGGAGA

TABLE 2-continued

TTGGAACAGGAGACCTCAAAGGGAGAAGCAGAAGGGAGAGTTATGAATCG
ATTTCCTCAGAAACTTTGATGAATATTTATTTATCTCCTTTAAGGTGTTT
TCTTCCCATGATCTTAAAAAGACTGGAAGTGGGTGGGAGTTTCAAAACCG
TGATGCAAATGACATTATGCGGAAGCCAGCATCTTTTGAAGATGCGGAAA
CTTTGTTAGTGTACATATGAGACAACTGTGCAGGTTTTCTGGGTGCTTTA
GTCTCTGAGATAGCAGCAGGAGTCTAACTACAGCTTTCAAGATGCTTAAA
TCACAAAGGTGCCATTGGACCATTGATAAACACAGTTTCCAAGGGCCAGC
TGCAAATTTTCTAGGTTACTTCATATTTAACTCTGTGCCTATTCAGGCTT
AATAAGTCTAGATTCTTGGCATGGTCACATTGAGAAGCCAGGAGTCCTGG
TTTTAGTCATATACCCCTATTTTTAACACTATGGAAAACACCAAAAATGG
TTCTTTTAAAGTAGTGGTTCTCAACTTGTGGATCTTGTCCCCTTTGGGGG
TTGAAAAACCCTTTTATAGGTGTCACATATGAAATATCCAGCCTATTTGA
TATTTACATTATGATTAATAATATTAGCAAAATTACAGTTATGAAATAGC
AATGAAAATAATTTTATGGTTGGAGGTCACCATCTATGAGGAACTACACT
ACAGGGTCGCAGCATTTGGAAGGCTGAAAACCACTGTTACAGAGTGTCCA
GACAGGGGCAGATGACTCTTCAATATTCTTGCACAGTTGCAATGGCTCGA
GCATTATAGAGCTCTCTATAGAAAAATCAAATTAATTCTTGAACACTCTA
GGACTTCAGAAAGTCAACACTTCAGAGGGAGTTTACCATAGAGTTCCTCT
GGGACATCAAAAAACCTAAGACAGTGTTTAGAGGCCTCTTCCATGACATA
CAGGGGTTGGCATAGTAGCTGTTTCCCCAAAGTGAGGTAACTTATAAGAA
CAGAGATAGACTCAAGAAACCTAGTTGGTCAGTGGCCTTTTGTATCTAAG
GAGAGATGGATGCTATTTTGCATCTCTTGGAACACATGGAAGCATTCAGA
CATGGGACCTCCTGGGCAGCCTGGATGTTCTGTCAGTCACCACAGGGCT
GAGCTGGTTGTTAGGTGGATGAGATTTAAGCACAGGTACATTTCATTCA
TAGGTGGCTCCATCAACTCCAGACTCTTATTATCTTTCAGGCTAATACAT
GGCTATTGTTAGTGAAGCCACCTTCATTTACAGGTTAGAGGTAGTCATGC
TTTCATGCTTTACGGATGGAGAGGACTCTATAAAACAGGATATTATATAC
AGTTCCTGAGAATAAGTGATAGTTTTGAGCCCTTAAAACAGTAAACTTCC
TGCTTGGTCTGTGTGGTGCTTCGGAAGCTGAGATAAGAAGATAGTGCTGG
CTAGCCTGGGCTACATAGTGAAACCTATTTATAAAACCAAATCAAACCAA
ACCAAACCAAACCAAACCAACAACAACAACAACAACAACAAACCC
CCCCCCCCAAAAAAACCCAAAAACCAAAAAACCAACCAACCAACCGAAC
AACAACAAAATCCAGTCAACTCACAATTTTCACTTAAGTGTTATACTGGC
TAAGTGCCATATGTCTGACCTAATGGTCTTTGCCTTAAACAATTAGCTGT
GTACACAGAGGGATTTCTTCCATGAAGTCTGAGGCAGGGCATCCTGTCCT
CTGAGGATTTTCTTGATCTACTCTAATCCTCTTTTCCTGCTAAGATGAAT
GAATGTAGACATCTGCGGAGTCAGTGAGACAACCGCACGATGATTGTTTC
AGAGCCTACGCTGTTTCCAGTCTTTGTCATTGAGTACACACACGGTGCAG
GTGCCCTGCGCACACACTGCCTGGTTGCTAACATCTTCTAAAGGCATTGG
AAATGGATGGGAGGCACTGGTGGGTTTCATTTCCTTTCGTGCTTGTCCTC

TABLE 2-continued

AACTCTCTGAAAAGTGTTTGGCTCAGCAGAGGTGTCCCAAGGATGCATGG
CTTAATTGTTCTTATAGCCTTTGCTGCTACCAGTCTGCCTCTGCCTCCCA
GTACAGGGAAGAGAGTGGGAAGATTGAGGACACGGGAGTCAATCAGTGTC
CTTCCTTCCACGTACCAGTGGATGAATGGACAATTTGAGTAAGACACATC
AGTTAAATGTAATCACAGTGTACGGCTGCAACGAAAGCAACTTCTAATTC
TGAAAGCCACAGCCAACAGGAAGCCAGTTCTTCTCAAAGGGGCAATAGCT
CTCATCAAAAGACATTTTCATTTGTAAAACTATAAAGTTGTTTGGAAAAT
GCGGACAGGATTTATTGGTCATGTGGAACCGAAGTGCCCTGATGTTCACT
GTGCTGCGCCGAGCCCTGCGAAAGAGCATTTGTAGGTAATGCTTCATAAT
GAAGTTGTTCTGCAGCCCAGAGAAAGAAAGAACTTACTCTGAAGGTCTTC
CACATCCTCTACCCTTCACGATCCATATATGAATCCATCTCGATCCGGAC
AACAGGGTTTTGTGGAAAACAAATTACGAGCACTTTGTCCCCTTTTGTTC
ATGTTGGTAAGGTTTCTTAATTGTGTTCCCAAACACAGAGGACCACAGCC
TTCCCCTCCAAGGGCTGTAAAGAATCGTGTGCACTTTGAAATTGTTAGAG
GGAATGCACTAAGAATATTGATGGGGAGGGCACTGGTTTGAGCGTTTTTC
AAGAAATTCTCACTCTTTGCTTGAGAAGGCAAAGGCAGAGAGAAATACAT
TGGATGGGCAAATAGATGCATCAGCCTGTTGACGACAGCCTCTGTGTTTT
AATGCTCGGCTCAAGGCAATTTCTGCTACCCCCTTCTCTGTCTCTGCCAG
TGGAACTATCTCTTAAATCAAGAACAAAATTTATAGGAGTATCATTTGAA
AACACTTACATTGGAGCCACCTTAGTTGTTTTTAAAAAATACTCATTTCT
AGATGTCATCTAGACTTAACAAGATAGAATGAAGGCCTATGTATCTGAAC
CTTCCATCAAGAGTCTAGAGACAGGTAGGTAGCATGTGGTAAGAAATGAC
CACTAACTTTTAACATCATTGAATTTATCTTGAAGACATAGTCATTCAGG
ATTCCTTACTGTTCTCAGTGCTAGGCATGTGGTGAGCTAAATGGAGCCAT
TGATGGCTCAAACAGTAATTATACTGGCTTTCCTGGCTTTCTAACGCCTG
CTTTGGGTTTAAGTATAACTATTAATACTGGTTCTTCGCACCCCCACCAG
CAATATTTATTTGCTGTGCATTGCTTTACTGTACTTTGTCGAAGGTGAAT
GAGTACTTTGTAAGCACTCTTCAATATACAGGCCCACCCCATTTCTCTGT
TGATACACAGTACCTGGCCTCAAAATGTCTCCCAACGAGTCCACAAATAG
TTGAGCGAGAGTCTCAATTACCTCTCCGCGCAGGTAATTATTACTTCTGC
CATTTAAGTGAAATTTCAGTACATTGCTTATAGAAACACATTTAGGAGCA
TATTTCTGCGGTACCTGCTTCTATTCACAGGGTAGATTTTAAAGTTCCAT
TTGTGTCATGGGAGAGAGCGCTAAACTGTCCTTTTGCATGAATTTGGCTG
ATAGTATATGAAATGTTAAGATGAGCTCATTTTCTCCCTCTACTTCTGTA
AGAGACTTAAAAAAGCCAAGCCAACAAACAAACCTCTTCCCTAGCACCCA
ATTTGCCTGCCGTAGGGAGGGTTCTATGTCTGTGGTCGACTAGTAACTGA
GAAGTTC

TABLE 3

SHORT ARM Sequence (2000 bp)

(SEQ ID NO: 2)
TTCTATGTCTGTGGTCGACTAGTAACTGAGAAGTTCTGTGGCTGCTCGCT

GAGCTAGGAAGTTTGCCGCCTTGGCACCTTGGAAGCCTCTTTATGGTCTT

GAATGAGTTCTGTGATATGTTTTGCAG<u>CATGCTCTTTCCGACAAGGCGTG</u>

<u>TGTGAAATCCTTTGACCCAAAGACGACCTGCTTGCAGGAATGCCTAATCA</u>

<u>CCACCTTTCAGGACGCTTACTTTGTTTCGGACAGTTTTGAAGAAGCCAAA</u>

<u>GAAAAGATGAGT</u>AAACCTGCTTTTCTTCCTTCTATAGAAAGTCACTTTTA

AATGTCTCTCGCTGTTCCTTCTGTCTAACTGTTTTTTGTACCCGTGGCGG

TTGATTGTGTTTTCCTTTTGTTTTTTTTTGTTTATTCTACAG<u>GGACTTT</u>

<u>GCAAAGTCAATTACCCATCCCTTCTCGGTATACTTCAACCCCTACACGCA</u>

<u>GAGCATTGAAATTCTGAAAGACACCAGAAGTATTGAGAATGTGGTGCAGG</u>

<u>ACCTGCGCAGTGATTTGAACACAGTGTGTGATGCCTTGAATAAAATGAAC</u>

<u>CAATATCTGGGGATTTGA</u>GCCTAGAACCAGAGTTATTGTCAGCATGAGCT

CTTGGGGGGTGTAGCAACAATGCAGTCAATGTTATCCAACATCAACAACT

TTCTGTGTCATGGTTGGCTAGTAAGCATGCAATTCTGTATGTCCATACCT

CTGTGTAACTTAATAACACAAAAATGCTCTAAAGAACCCATGCAGATAAC

CACTCACCATTTGAAAGATTGTGATCCTATTTGGACATCTCAAGTAGAGT

TGACATTTCTGATTAGCGAACAAACTGTTAACTTAAGCAAACTGTGACTT

TGAAATCTGTAGCAAACATTCCTCGCACAATTCCAGTCGGTGAGTTGTGG

AACTTTTCTTCCTTGGACCTGAGACTTTCCTCTGTGTTCATTAGATAAAA

TGAAAATAGTTGGGAGGTGGTTTCTATTTTCAATAGTATCCGTGTTATTT

GAGATAAACTAGAGTTGCTCCACGCTTTGCATCACAGCAACAAAGGATTT

AATATTCTACTTCAGAAGCTGTTCAGAAACACAGCAGTTGGGATGGATGT

AGACTGAGTGTTCAGACAATGCAAGCAAAGAAAAGTTTTGATAAACAGGA

TATATAGGTTGTACTGACCTCGTTGAAACCAATTTGTGGCAAGCTTCCTG

AAGAGCTTCTGGAAGGAAACACTTGAACAAAGAATATTCGGGAAGCTTAA

ACAGAAGGGATGAAAATCTTGGAACTGTGAATGTATTGTTAGGATAGAGT

GAATTATCACTGCAGGCTTTTGACTCCTTTTGCTTAGACTGAGAACCTCA

AATCCCACAGGGATGTAAATACCATCTCTGATTCCAAAGAGTTGGAGACG

GAGTCGTAGAGAAACAAAGGGATTTGCTTCAGTTAGGTCTGATGAGATGT

GCCATGGTCATAAGCCACTGCCCTTTTATGTTGGACATCTGACAAGTCTA

CTGTAGTGTACATGCATGTTTATGTATTGACACAGAAAGAAAATTATTGC

TTATAAAATGAATGCTTCTCAATAAACAGAATCTTGCCCCCAACAGGGTA

TCTCTTATCTCATCTCACACCTTGAAAACAGGCTCTGTCTATGGGAGGG

AGATTTTTCTCAAAATCTGGGGCAACTCTGGGTAAACAATAGTGATTTGC

TGTAAATGTCTGGTGATTTTTGCTATAAAAGATAAAAAGCAAACGAACAT

TCTCCCCTCCCCCCAAAAATCCCAAGTGTCTAAGTGAGCAAGTGAAAAAC

TGCTGAATCAGTTAATTTAATTATCTTCAAATGGGTTCCCTCATCGAACA

AGCCTCCTAATTCTGCTCCTTTTGGGAAGCAGTGCAGGGGCTGGACAGAG

TABLE 3-continued

TGGGAGGGGTAGGGGCGAGAGGTATAGAAGGAGACAGAAAAAAAACTTTT

AAGTTAGAGTATTGGCTAGTTTTCTATTCCTGTGATAAAACACCATGACC

Exons are underlined, the mutated base is in bold.

The targeting construct was transfected into 129S6/SvEv mouse ES cells. Clones carrying recombinant mTph2 alleles were selected using a standard diphtheria toxin (DT)/G418 double selection protocol. Positive ES cell clones were subsequently karyotyped and occurrence of homologous recombination confirmed by PCR. Four recombinant ES cell lines were then transiently transfected with a CRE recombinase expression construct to remove the TK/NEO selection cassette (FIG. 1B). Ganciclovir negative selection followed by PCR amplification using primers (5'-CACCCAATTTGCCG-TAGGGA (SEQ ID NO: 3); 5'-GCTGCAAAACATATCA-CAGAACTCATTCAAGACCA (SEQ ID NO: 4)) flanking the TK/NEO cassette were used to select clones lacking the selection cassette.

A G-allele/A-allele specific ARMS-PCR protocol was used to confirm the presence of the G1449A mutation in the selected ES cell clones used to generate chimeric mice. The following primers were used for ARMS-PCR: mOuter/Forward primer, (5'-TGGTCTTGAATGAGTTCTGTGATAT-GTTTTGCA (SEQ ID NO: 5)); mOuter/Reverse primer, (5'-TCATGCTGACAATAACTCTGGTTCTAGGC (SEQ ID NO: 6)); G-allele specific primer, (5'-TAGGGGTTGAAG-TATACCGAGAAGGCAC (SEQ ID NO: 7)); A-allele specific primer, (5'-TAGGGGTTGAAGTATACCGAGAAG-GCAT (SEQ ID NO: 8)).

Chimeras were intercrossed with C57BL6/J or 129S6/SvEv mice and offspring (F1) that inherited a mutant Tph2 allele were identified by PCR analysis (FIG. 1C). Finally, expression and integrity of the mutant Tph2 transcripts in (F1) mice carrying the engineered A-allele was confirmed by rtPCR cloning of brainstem Tph2 full length mRNA followed by sequencing.

Example 2

Evaluation of serotonin synthesis in the brain of Tph2 R439H knockin mice. For all experiments involving knock-out or knock-in animals, respective WT littermates were used as controls, and all mice were 3-4 months of age. Before experiments, animals were housed 4-5/cage in a humidity-controlled room at 23° C. with a 12 hr light/dark cycle with ad libitum access to food and water. Experiments were conducted with an approved protocol from the Duke University Institutional Animal Care and Use Committee and experiments conducted according to National Institutes of Health guidelines.

Methods used to analyze levels of 5-HT and 5-HTP using HPLC and electrochemical detection were as described (Zhang et al., 2004, Science 305:217). The 5HT synthesis rate in vivo was measured in mice treated with 100 mg/kg (i.p.) of m-hydroxybenzylhydrazine (NSD-1015) for 1 hr (Zhang et al., 2004, Science 305:217). Data from neurochemical studies and western blot were analyzed by two-tailed t-tests. ANOVA or repeated measures ANOVA (RMANOVA) with Bonferroni tests were applied for behavioral studies using the Statistical Package for the Social Sciences (SPSS), Version 11.0 (Chicago, Ill.). Normal distribution of sample population was assessed by chi-square.

Figure 2:
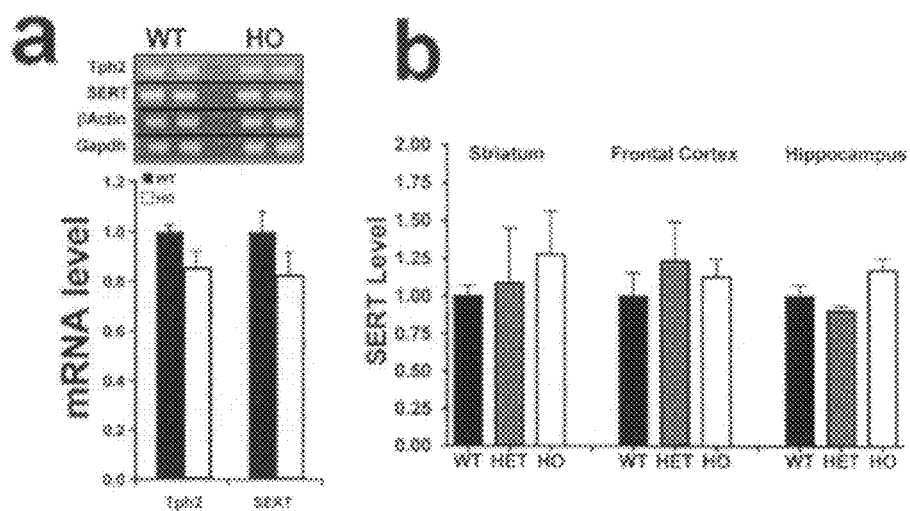
FIG. 2. Expression levels of Tph2 transgene. (a): Semi-quantitative rt-PCR of Tph2, SERT, β-actin, and Gadph mRNA levels in the brainstem of WT and HO R439H Tph2 mice (n=4 mice/group). (b): Densitometric western blot analyses of SERT expression in different brain areas of WT, HET and HO Tph2 knock-in mice. Data are normalized to optical densities for WT animals, β-actin was used as a loading control (n=4 mice/group). Data are means±SEM.

Mice carrying the R439H Tph2 mutation developed without overt phenotypes and reproduced normally. Semi-quantitative RT-PCR analysis of Tph2 mRNA in homozygous (HO) R439H Tph2 mice showed no changes of Tph2 gene expression as compared to wild type (WT) littermates (FIG. 2) and sequencing of PCR products confirmed the integrity of the mutated R439H Tph2 transcript. Expression of the 5HT transporter (SERT), a target of most antidepressants and a potential contributing factor in the development of mood disorders, was also unaffected in these mice as measured by RT-PCR and western blots (FIG. 2).

Figure 4:
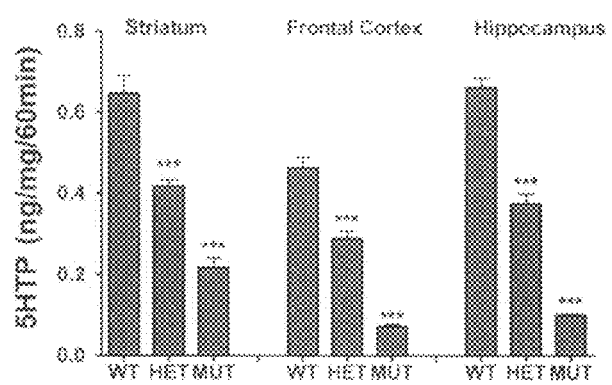
FIG. 4. Reduced 5-HT synthesis in Tph2 knockin mice. 5-HTP synthesis as measured by HPLC (Zhang et al., 2004) in the striatum, frontal cortex and hippocampus of WT, heterozygote (HET) and homozygote (MUT) Tph2 R439H mice 60 mins after administration of m-hydroxybenzylhydrazine. (***$P \leq 0.001$).

The effect of the R439H mutation on 5-HT brain tissue content and synthesis in vivo was evaluated. Monitoring the accumulation of the 5-HT precursor and Tph2 product, 5-HTP, following treatment of mice with the aromatic amino acid decarboxylase inhibitor, m-hydroxybenzylhydrazine, provides a direct assessment of Tph2 activity in vivo (Zhang et al., 2004, Science 305:217). As shown FIG. 4, synthesis rates in the frontal cortex (FC), hippocampus and striatum were reduced by ~40% and ~80% in heterozygous (HET) and homozygous (MUT) R439H Tph2 knock-in mice, respectively.

Figure 3:
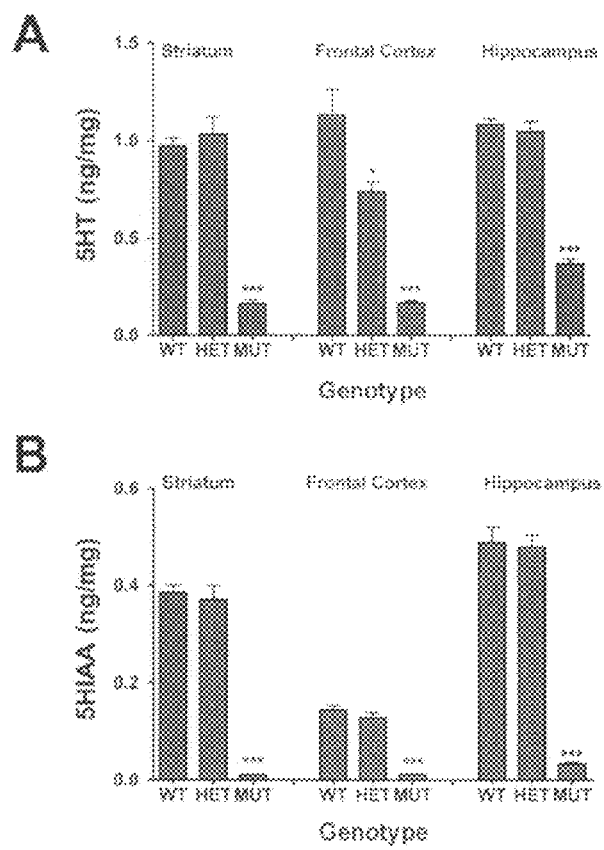
FIG. 3. Reduced 5-HT storage in Tph2 knockin mice. A: 5-HT tissue content as measured by HPLC (Zhang et al., 2004) in the striatum, frontal cortex and hippocampus of WT, heterozygote (HET) and homozygote (MUT) Tph2 R439H mice. B: 5HIAA tissue contents for these same extracts. (*$P \leq 0.05$, *** $P \leq 0.001$).

As a result of decreased synthesis, tissue contents of 5-HT were also substantially reduced in these same brain areas of MUT R439H mice (FIG. 3A). However, in HET R439H Tph2 knock-in mice a significant reduction in 5-HT content was only apparent in frontal cortex, suggesting that the homeostatic control of 5-HT levels may differ among various brain regions. Finally, measure of tissue levels of the 5-HT degradation product 5-hydroxyindoleacetic acid (5HIAA) showed no differences between WT and HET R439H mice, while 5HIAA was reduced to almost undetectable levels in all tested brain regions in homozygote Tph2 knock-in mice (FIG. 3B). Taken together, these neurochemical data indicate that the R439H mutation substantially reduces Tph2 activity in vivo and provide further direct evidence for the critical role of this enzyme in the regulation of brain 5HT synthesis.

Example 3

R439H knock-in mice exhibit behavioral differences in tests used to assess the actions of antidepressants. Assessment of "behavioral despair" is the most common approach used to assess actions of antidepressants in mice (Crowley et al., 2004, Pharmacol. Biochem. Behav. 78:269-274; Lucki et al., 2001, Psychomparmacology (Berl) 155:315-322). In the Porsolt forced-swim and the tail-suspension tests, drug-induced reductions in immobility times are predictive of antidepressant activities of drugs.

Tail suspension test: Mice were tested in a tail suspension apparatus (Med-Associates, St. Albans, Vt.) as described (Crowley et al., 2004, Pharmacol. Biochem. Behav. 78:269-274). All mice were weighed and tail-marked 24 hrs before testing. Animals were brought into the testing room 4 hrs before injections. Pilot studies were used to determine the optimal automated threshold settings for immobility by comparing scores rated manually with scores tabulated simultaneously by the apparatus. Behavior was scored as time spent in immobility (sec) for the total period of the test.

Forced-swim test: Animals were tested in forced-swim test as described for mice (Lucki et al., 2001, Psychomparmacology (Berl) 155:315-322). Animals were weighed, tail-marked, and brought into the test room as described above. Swimming sessions were conducted in a Plexiglas beaker (20×51 cm) filled to a depth of 40 cm with water maintained at approximately 25° C. Mice were gently placed into the beakers and allowed to swim for 6 min. All tests were videotaped and scored using the Noldus Observer (Noldus Information Technology, Blacksberg, Va.). Immobility time was scored as the absence of struggling and escape-related behaviors.

Figure 5:
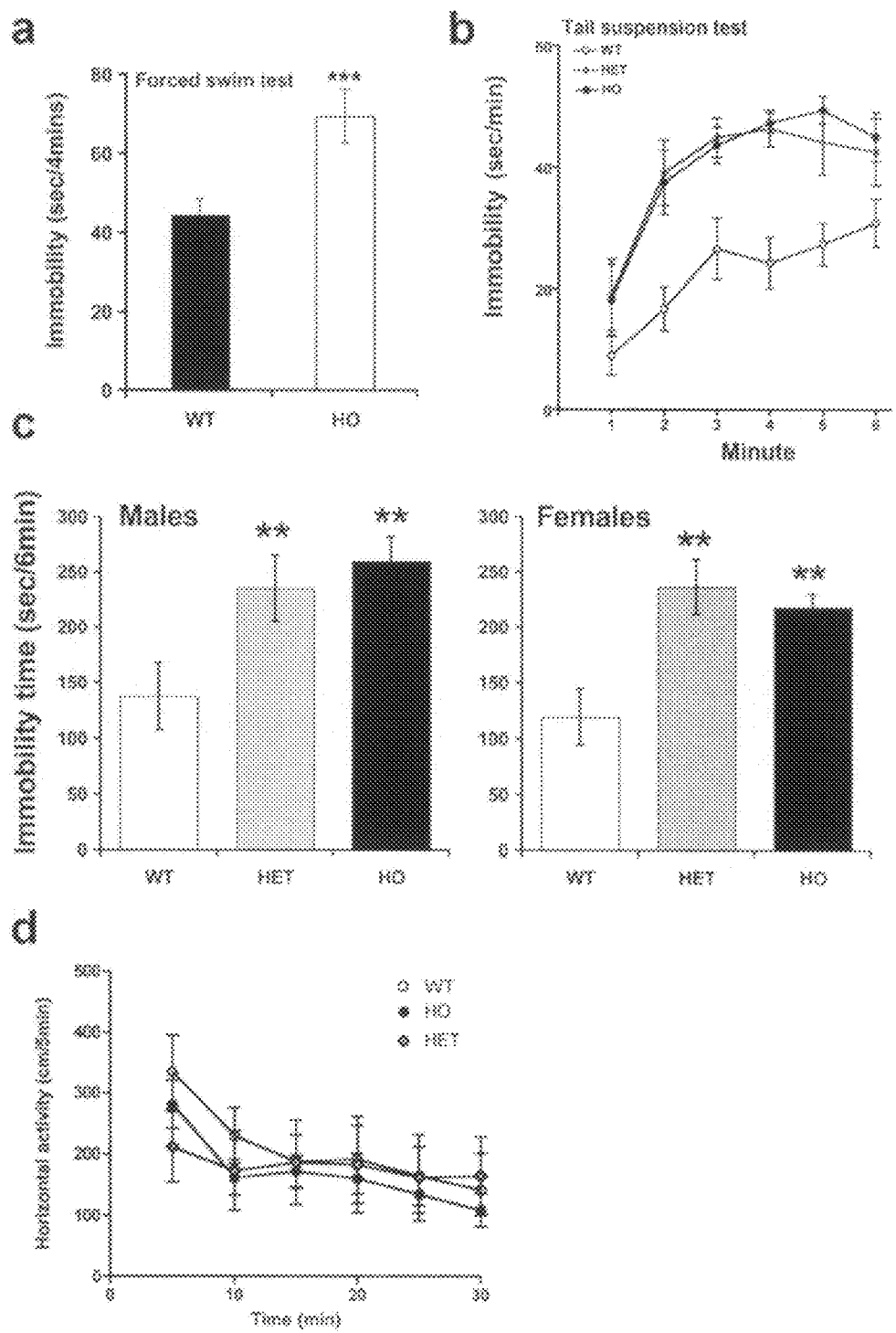
FIG. 5. Enhanced behavioral despair in R439H Tph2 mice. (a) Immobility times in the forced-swim test for naive WT (n=16) and HO Tph2 mice (n=15 mice). (b,c), Immobility times in the tail suspension test for naive WT (n=10, 5 males, 5 females), HET (n=10, 5 males, 5 females) and HO (n=11, 6 males 5 females) R439H Tph2 mice. Data for the whole group are presented for each minute of testing in Panel b. Total immobility time for the whole duration of the test is presented for mice of each sex in panel c. (d) Basal locomotor activities of WT (n=10), HET (n=9), and HO (n=10) Tph2 mice. Mice were placed into the open field and locomotion was measured in 10 min segments over 30 min. Data are shown as average±SEM. *$p \leq 0.05$, ***$p \leq 0.005$ as compared to WT mice ANOVA followed by Bonferroni corrected pair-wise comparisons. Statistical significance ($p \leq 5.05$) was established by RMANOVA in Panel b.

HO R439H Tph2 mice displayed marked enhancement of immobility in the forced-swim test. Furthermore, HO and HET R439H Tph2 mice from both sexes showed equally increased immobility times in the tail suspension test as compared to WT littermates (FIG. 5).

Measurement of open field activity: Because changes in general activity can affect results from these tests, basal locomotor activity in the open field was monitored in the three genotypes of mice. Locomotion was evaluated under illuminated conditions in an automated Omnitech Digiscan apparatus (AccuScan Instruments, Columbus, Ohio). Mice were placed into the open field and activity was monitored for 30 min after injection. Activity was measured in terms of the total distance traveled (horizontal activity) (Beaulieu et al., 2004, Proc. Natl. Acad. Sci. 101:5099-5104). No differences in basal locomotion were detected among mice from these genotypes (FIG. 5). These data indicate that reduced 5-HT synthesis in R439H Tph2 mice does not affect general motor activity, but instead results in specific enhancements in immobility times in tests used to assess antidepressant drug action.

Example 4

Reduced reward to a natural reinforcer in R439H Tph2 mice. Reduced reward and loss in the ability to experience pleasure (anhedonia) is a major endophenotype of depression in humans. We assessed the effects of reduced brain 5-HT synthesis on operant responding for sweetened condensed milk reward, a subjectively pleasant, natural reinforcer (Caine et al., 1999, Psychopharmacology (Berl) 147:22-24).

The operant reward protocol was adopted with modifications from previously described procedures (Caine et al., 1999, Psychopharmacology (Berl) 147:22-24). Singly-housed mice were tested during the light phase of the diurnal cycle in 2 hr sessions 7 times a week. Experimental chambers (~23×12×19 cm) were equipped with a house light, ventilator fan and two levers with cue lights that were located adjacent and on each side of a liquid dipper equipped with a 17 µL cup (Med Associates Georgia, Vt., USA). The liquid reward consisted of Eagle Brand & Borden condensed milk (Eagle Family Foods, Gahanna, Ohio) diluted in sterile water (396 grams in 2 L). In the first phase of operant testing, food-deprived (24 hours) mice learned to press a lever for condensed-milk reward. Training was facilitated by Pavlovian autoshaping. Once mice reached the criterion (40 rewards/session), mouse chow was provided ad libitum in the home cage. The initial acquisition was robust and comparable between genotypes (data not shown). During subsequent sessions, condensed milk was available under a fixed ratio 1 schedule of reinforcement. Once an animal's response-rate variabilities were within 20% across three consecutive sessions, water was substituted for the condensed milk for five subsequent sessions. This resulted in a rapid and comparable extinction of lever pressing in both HO R439H Tph2 mice and WT littermates (FIG. 4a).

To further establish that lever pressing was a function of the availability of reward, undiluted condensed milk and water were made available alternately over six sessions. As shown (FIG. 4b), operant responses were higher and comparable across genotypes when condensed milk was available. Results from this phase of testing indicate that control WT littermate and HO R439H Tph2 mice do not differ in acquisition of operant behavior for food reward, extinction of this behavior, or distinguishing between water and sweet reward.

Figure 6:
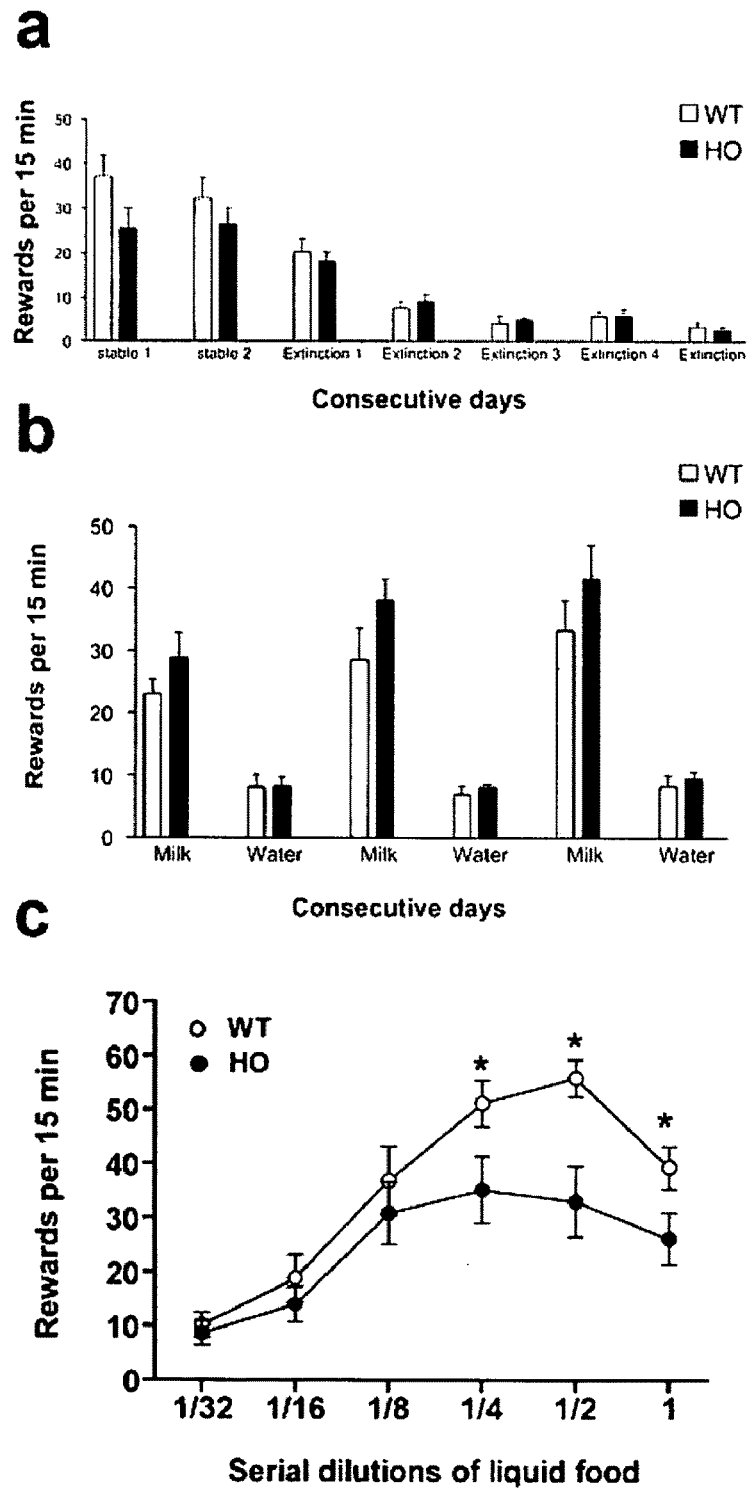
FIG. 6. Reduced operant responding for a natural reinforcer in R439H Tph2 mice (a,b) Similar extinction rate (a) and ability to distinguish between water and sweetened condensed-milk reward (b) in WT and HO Tph2 mice. (c), Lever pressing rates for various dilutions of sweetened condensed-milk reward in WT and HO Tph2 mice. (n=6 mice/genotype). Data are shown as the mean number of lever presses±SEM during the first 15 min of the test session. *$p \leq 0.05$, ***$p \leq 0.005$ WT versus HO performance; ANOVA followed by Bonferroni corrected pair-wise comparisons.

In a subsequent phase of the testing, serial dilutions of condensed milk (undiluted, ½, ¼, ⅛, 1/16, 1/32 dilutions) were made available in a pseudo-random order over the next six sessions. Importantly, while exposure to various dilutions of sweet condensed milk caused both WT and HO R439H Tph2 mice to display inverted U-shaped responses to the reward, Tph2 knock-in mice manifested drastically reduced lever pressing for the sweetened condensed milk (FIG. 6). These data strongly point toward a reduction of reward in Tph2 knock-in mice and suggest that serotonin may contribute to the rewarding properties of natural stimuli.

Example 5

Administration of anti-depressants or glycogen synthase kinase 3 inhibitors alleviates behavioral differences. Fluoxetine (Tocris Cookson Inc., Ellisville, Mo.) was dissolved in distilled water. Thiadiazolidinone (TDZD) (Calbiochem, Cambridge, Mass.) was injected (i.p.) following suspension in a minimal amount of Tween and diluted to volume with distilled water as previously described (Beaulieu et al., 2004, Proc. Natl Acad. Sci. USA 101:5099-5104). Corresponding vehicle solutions were injected in control animals. Mice were treated with vehicle or drug 30 min before testing. Behavioral testing was performed as described above.

Figure 7:
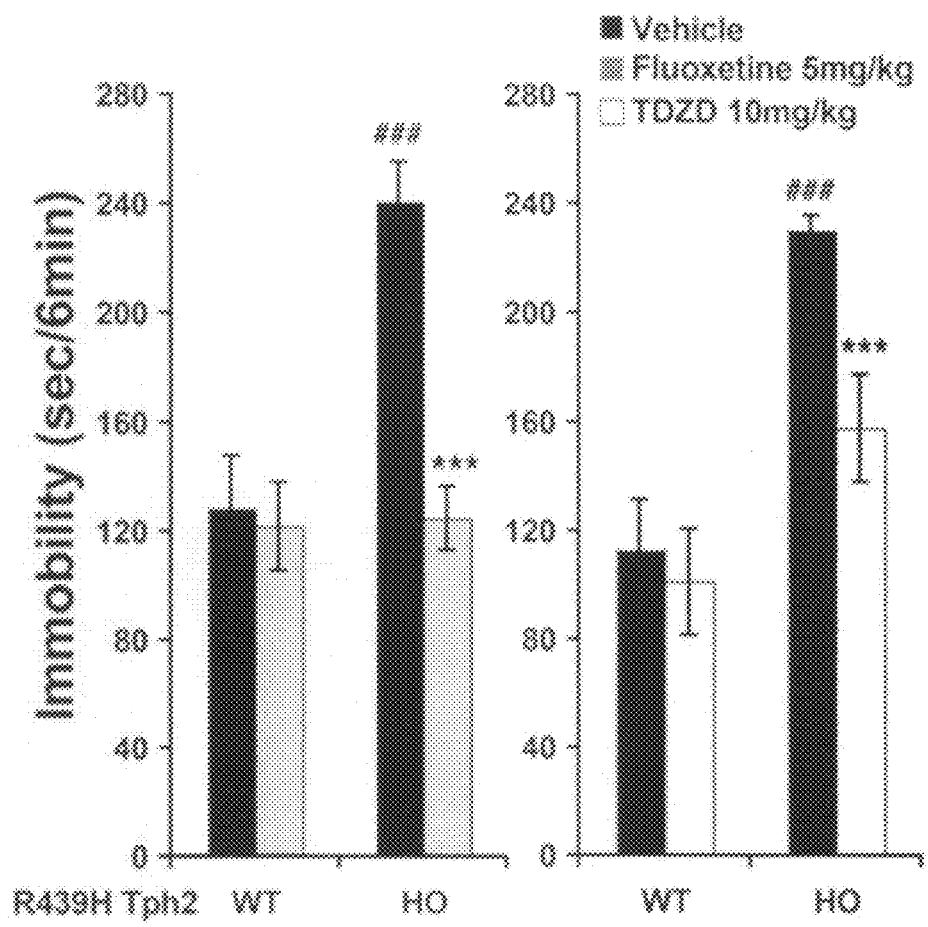
FIG. 7. Administration of antidepressants or glycogen kinase 3 inhibitors rescues depression-related behavioral abnormalities in Tph2 knock-in mice. Tail suspension test in WT and HE R439H Tph2 mice 30 min following administration of vehicle, fluoxetine (5 mg/kg), or TDZD (10 mg/kg). ***: $P \leq 0.005$ from vehicle control within genotype, ###: $P \leq 0.005$ from WT littermates. ANOVA followed by Bonferroni corrected planned comparisons.

As shown in FIG. 7, administration of the blood brain barrier-permeable glycogen syntase kinase 3 inhibitor thiadiazolidinone (TDZD) or fluoxetine to HO Tph2 knock-in mice resulted in a comparable reduction of immobility times in the tail suspension test.

Example 6

Figure 8:
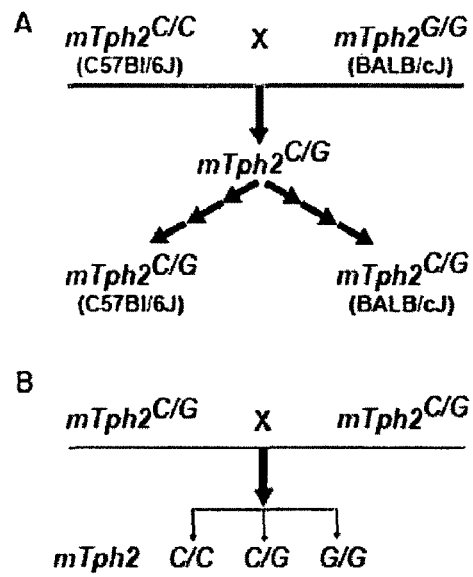
FIG. 8. Generation of congenic mouse lines carrying either 1473C or 1473G allele in Tph2. A: Backcross breeding of C57B1/6J carrying homozygous 1473C and BALB/CJ carrying homozygous 1473G in Tph2. B: Using C57B1/6J or BALB/cJ mice carrying heterozygous 1473C/G to generate congenic mice carrying 1473C/C, 1473C/G and 1473G/G alleles in Tph2.
Figure 9:
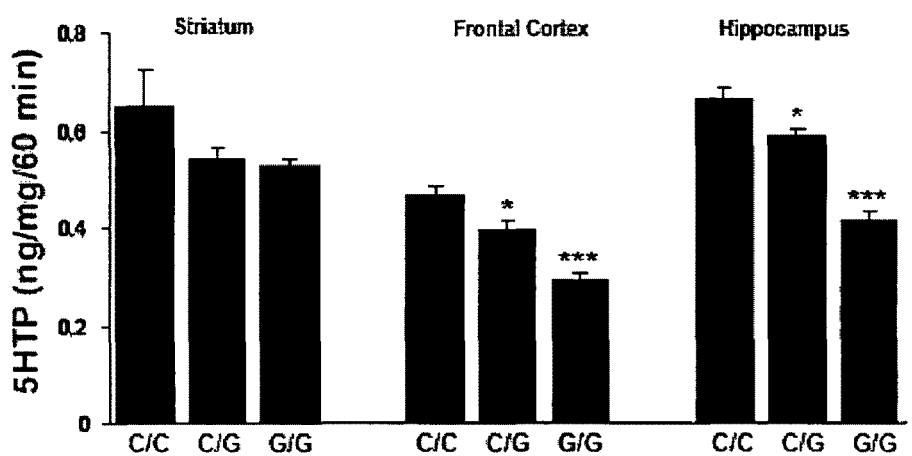
FIG. 9. Reduced rate of 5-HT synthesis in congenic mice carrying either 1473C or 1473G allele in Tph2. 5-HTP synthesis was analyzed by HPLC (Zhang et. al., 2004) as a measurement of the rate of 5-HT synthesis in the striatum, frontal cortex and hippocampus of congenic mice carrying C/C, C/G and G/G alleles in mTph2. (*: $P \leq 0.05$, ***: $P \leq 0.001$).

Generation of congenic mice carrying Tph2 mutants. We have applied backcross breeding strategy to generate congenic mice carrying the functional (C1473G) (Zhang et al., 2004) SNP, which exhibited ~50% reduction in 5-HT synthesis when the C allele in mTph2 was replaced with the G allele (FIG. 8). To determine the rate of 5-HT synthesis, congenic mice carrying homozygous 1473C/C (C/C), heterozygous 1473C/G (C/G) and homozygous 1473G/G (G/G) were treated with m-hydroxybenzylhydrazine for 60 min to determine the accumulation of 5-HTP. Significant and progressive reduction in 5-HTP in the frontal cortex and hippocampus, but not striatum, was observed in these mice (FIG. 9).

These congenic mouse lines will allow one to study the role of brain 5-HT while minimizing the potential contribution of other modifier genes. Similar techniques are used to create congenic mice carrying other functional mTph2 alleles.

Example 7

Testing of aggressive behavior in Tph2 mutant mice. Aggressive behavior is tested in mice using a model of spontaneous intermale aggression as described (Kulikov et al., 2005, Genes, Brain and Behav. 4:482-485). Intermale aggression is measured in encounters between pairs of males using two indices: 1) the level of aggressiveness, using the percentage of mice attacking, and 2) intensity of the aggression, measured by the number of attacks. Comparisons are made between wild type, heterozygous and homozygous Tph2 mutant mice. Mice are also tested and compared using other behavioral models, e.g., the resident intruder test, the zero maze test (see, e.g., Cook et al., 2002, Beh. Genet. 32(2):113-118) and novelty induced hypophagia tests (see, e.g., U.S. Patent Application Publication No. 20050186137), as known in the art.

The foregoing is illustrative of the present invention, and is not to be construed as limiting thereof. The invention is defined by the following claims, with equivalents of the claims to be included therein.

That which is claimed is:

1. A transgenic mouse comprising a mouse R439H mutant tryptophan hydroxylase 2 (Tph2) transgene, which replaces endogenous Tph2 in the genome of said mouse, wherein said mouse is homozygous for the transgene, wherein said transgene results in reduced synthesis of 5-hydroxytryptophan (5-HTP) and reduced levels of serotonin in the brain of said mouse as compared to a wild-type mouse, and wherein said mouse exhibits a behavioral phenotype of a serotonergic neurotransmission dysregulation disorder as compared to a wild-type mouse.

2. The transgenic mouse of claim 1, wherein said serotonergic neurotransmission dysregulation disorder is depression.

3. The transgenic mouse of claim 2, wherein the behavioral phenotype of depression comprises behavioral despair.

4. The transgenic mouse of claim 3, wherein the behavioral despair is evidenced by increased immobility in a tail suspension test as compared to a wild-type mouse.

5. The transgenic mouse of claim 4, wherein the increased immobility can be reduced by administration of thiadiazolidinone.

6. The transgenic mouse of claim 4, wherein the increased immobility can be reduced by administration of fluoxetine.

7. The transgenic mouse of claim 1, wherein the synthesis rate of 5-HTP is reduced by at least 70% in the brain of said mouse as compared to a wild-type mouse.

8. The transgenic mouse of claim 1, wherein said transgene results in synthesis of 5-HTP in the frontal cortex and hippocampus of said mouse as compared to a wild-type mouse.

9. The transgenic mouse of claim 1, wherein the synthesis rate of serotonin is reduced by at least 80% in the brain of said mouse as compared to a wild-type mouse.

10. The transgenic mouse of claim 1, wherein said transgene results in reduced levels of serotonin in the frontal cortex and hippocampus of said mouse as compared to a wild-type mouse.

11. The transgenic mouse of claim 1, wherein said transgene results in increased immobility in a tail suspension test as compared to a wild-type mouse.

12. The transgenic mouse of claim 11, wherein said transgene does not result in a decrease in basal locomotion measured by an open field test as compared to a wild-type mouse.

13. The transgenic mouse of claim 11, wherein said transgene results in reduced lever pressing in an operant behavior for food reward test as compared to a wild-type mouse.

14. The transgenic mouse of claim 1, wherein said mouse is an adult.

15. A progeny mouse of the transgenic mouse of claim 1.

16. The mouse of claim 15, wherein said mouse is a congenic mouse.

17. A cell isolated from the transgenic mouse of claim 1, wherein said cell comprises said transgene.

18. The cell of claim 17, wherein said cell is a central nerve cell.

19. A cell culture produced by culturing the cell of claim 17.

20. A cell culture produced by culturing the cell of claim 18.

21. A transgenic mouse comprising a mouse R439H mutant tryptophan hydroxylase 2 (Tph2) transgene, which replaces endogenous Tph2 in the genome of said mouse, wherein said mouse is heterozygous for the transgene, wherein said transgene results in reduced synthesis of 5-hydroxytryptophan (5-HTP) and reduced levels of serotonin in the brain of said mouse as compared to a wild-type mouse, and wherein said mouse exhibits a behavioral phenotype of a serotonergic neurotransmission dysregulation disorder.

22. The transgenic mouse of claim 21, wherein said serotonergic neurotransmission dysregulation disorder is depression.

23. The transgenic mouse of claim 22, wherein the behavioral phenotype of depression comprises behavioral despair.

24. The transgenic mouse of claim 23, wherein behavioral despair is evidenced by increased immobility in a tail suspension test as compared to a wild-type mouse.

25. The transgenic mouse of claim 21, wherein the synthesis rate of 5-HTP is reduced by at least 40% in the brain of said mouse as compared to a wild-type mouse.

26. The transgenic mouse of claim 21, wherein said transgene results in reduced synthesis of 5-HTP in the frontal cortex and hippocampus of said mouse as compared to a wild-type mouse.

27. The transgenic mouse of claim 21, wherein the synthesis rate of serotonin is reduced by at least 40% in the brain of said mouse as compared to a wild-type mouse.

28. The transgenic mouse of claim 21, wherein said transgene results in reduced levels of serotonin in the frontal cortex of said mouse as compared to a wild-type mouse.

29. The transgenic mouse of claim 21, wherein said transgene results in increased immobility in a tail suspension test as compared to a wild-type mouse.

30. The transgenic mouse of claim 29, wherein said transgene does not result in a decrease in basal locomotion measured by an open field test as compared to a wild-type mouse.

31. The transgenic mouse of claim 21, wherein said mouse is the progeny of a transgenic mouse expressing a mutant Tph2 transgene.

32. The transgenic mouse of claim 21, wherein said mouse is an adult.

33. A progeny mouse of the transgenic mouse of claim 21.

34. The mouse of claim 33, wherein said mouse is a congenic mouse.

35. A cell isolated from the transgenic mouse of claim 21, wherein said cell comprises said transgene.

36. The cell of claim 35, wherein said cell is a central nerve cell.

37. A cell culture produced by culturing the cell of claim 35.

38. A cell culture produced by culturing the cell of claim 36.

39. A method of screening a compound for serotonergic activity, comprising:
    administering a test compound to a transgenic mouse according to claim 1; and then
    detecting, in said mouse, the presence or absence of serotonergic activity in a biochemical assay or behavioral test.

40. The method of claim 39, wherein said compound is a selective serotonin reuptake inhibitor.

41. The method of claim 39, wherein said detecting step is carried out by performing a behavioral test selected from the group consisting of a tail suspension test, a forced swim test, a learned helplessness test, a fear conditioning test, a resident intruder test, a water maze test, a radial maze test, an operant conditioning test, a self-administration test, an open field locomotion test, a place preference test, a zero maze test, a latency to feeding test, a shock escape test and an open field exploration test.

42. A method of screening a compound for activity in treating a serotonergic neurotransmission dysregulation disorder, comprising:
    administering a test compound to a transgenic mouse according to claim 1; and then
    detecting, in said mouse, the presence or absence of activity in treating a serotonergic neurotransmission dysregulation disorder.

43. The method of claim 42, wherein said compound is a selective serotonin reuptake inhibitor.

44. The method of claim 42, wherein said detecting step is carried out by performing a behavioral test selected from the group consisting of a tail suspension test, a forced swim test, a learned helplessness test, a fear conditioning test, a resident intruder test, a water maze test, a radial maze test, an operant conditioning test, a self-administration test, an open field locomotion test, a place preference test, a zero maze test, a latency to feeding test, a shock escape test and an open field exploration test.

* * * * *

UNITED STATES PATENT AND TRADEMARK OFFICE
CERTIFICATE OF CORRECTION

| | | |
|---|---|---|
| PATENT NO. | : 8,124,831 B2 | Page 1 of 1 |
| APPLICATION NO. | : 11/825202 | |
| DATED | : February 28, 2012 | |
| INVENTOR(S) | : Caron et al. | |

It is certified that error appears in the above-identified patent and that said Letters Patent is hereby corrected as shown below:

In the Patent:

Column 3, Line 63: Please correct "($p \leq 5.05$)" to read -- ($p \leq 0.05$) --

Column 16, Line 45: Please correct "Eagle Brand &" to read -- Eagle Brand® --

Signed and Sealed this
Twenty-ninth Day of May, 2012

David J. Kappos
*Director of the United States Patent and Trademark Office*

SEQUENCE LISTING

<160> NUMBER OF SEQ ID NOS: 8

<210> SEQ ID NO 1
<211> LENGTH: 4657
<212> TYPE: DNA
<213> ORGANISM: Mus musculus

<400> SEQUENCE: 1

```
tttccctcaa aatctaacca gtcctaatat agagagtgag gataacaggt ttacatctac      60
aatagttgag atcatacctc tgtgtccctg tagaaatggg tgtctgagag gaaggaagat     120
gtcaagtgag tcagagaagc cacaattgca gtttgagtct tacaagtctc atacccggga     180
ccattctttc cctatagttc tagacctcgg ggggcgaggg aggacatgct tattaggcag     240
cacatacaat cctctctgga ctgaattagg gatggtaact aaatatgtta agcacgtccc     300
atgatagcca tttgcatgca tttcccgttt aattctgacc acaaccttgg gctatcgagt     360
ccattaggtt ccccaaactg tacaggaagg aacagagcca aatttaacct ccaagattga     420
gatgtaggct ctgaattatc ttgtattatt attccagcaa ctggaaaatt ttgatgtcaa     480
aaggatagtg accaatacca agtaactggt acttggtggt caagggtgac atgggttacc     540
tcaggaccaa taggaaaggc agcattggta aattgacaca ggcaaagtgg agagtgctct     600
gggtttatag gtcttgttaa aattatactg caagaagatt cttagattca tgcaggccag     660
```

-continued

| | |
|---|---|
| agtattttag atttaccaca gaggaaactg cagctcattt tgagatactt cctcatctgg | 720 |
| tattacactg ttactgggtt aaaaatttct cttcagttct tgtgttcttg aaggaaagaa | 780 |
| ttcagttgag aaacagttag atcaagtaga agtttattta gcaaagaagt gtagatactc | 840 |
| caaagggaga ttggaacagg agacctcaaa gggagaagca aagggagag ttatgaatcg | 900 |
| atttcctcag aaactttgat gaatatttat ttatctcctt taaggtgttt tcttcccatg | 960 |
| atcttaaaaa gactggaagt gggtgggagt tcaaaaccg tgatgcaaat gacattatgc | 1020 |
| ggaagccagc atcttttgaa gatgcggaaa ctttgttagt gtacatatga gacaactgtg | 1080 |
| caggttttct gggtgcttta gtctctgaga tagcagcagg agtctaacta cagctttcaa | 1140 |
| gatgcttaaa tcacaaaggt gccattggac cattgataaa cacagtttcc aagggccagc | 1200 |
| tgcaaatttt ctaggttact tcatatttaa ctctgtgcct attcaggctt aataagtcta | 1260 |
| gattcttggc atggtcacat tgagaagcca ggagtcctgg ttttagtcat atacccctat | 1320 |
| ttttaacact atgaaaaaca ccaaaaatgg ttcttttaaa gtagtggttc tcaacttgtg | 1380 |
| gatcttgtcc cctttggggg ttgaaaaacc cttttatagg tgtcacatat gaaatatcca | 1440 |
| gcctatttga tatttacatt atgattaata atattagcaa aattacagtt atgaaatagc | 1500 |
| aatgaaaata atttatggt tggaggtcac catctatgag gaactacact acagggtcgc | 1560 |
| agcatttgga aggctgaaaa ccactgttac agagtgtcca gacagggca gatgactctt | 1620 |
| caatattctt gcacagttgc aatggctcga gcattataga gctctctata gaaaaatcaa | 1680 |
| attaattctt gaacactcta ggacttcaga aagtcaacac ttcagaggga gtttaccata | 1740 |
| gagttcctct gggacatcaa aaacctaag acagtgttta gaggcctctt ccatgacata | 1800 |
| caggggttgg catagtagct gtttccccaa agtgaggtaa cttataagaa cagagataga | 1860 |
| ctcaagaaac ctagttggtc agtggccttt tgtatctaag gagagatgga tgctattttg | 1920 |
| catctcttgg aacacatgga agcattcaga catgggacc tcctgggcag cctggatgtt | 1980 |
| ctgtcagtca ccacagggct gagctggttg ttaggtggat gagattttaa gcacaggtac | 2040 |
| atttcattca taggtggctc catcaactcc agactcttat tatctttcag gctaatacat | 2100 |
| ggctattgtt agtgaagcca ccttcattta caggttagag gtagtcatgc tttcatgctt | 2160 |
| tacggatgga gaggactcta taaaacagga tattatatac agttcctgag aataagtgat | 2220 |
| agttttgagc ccttaaaaca gtaaacttcc tgccttggtct gtgtggtgct tcggaagctg | 2280 |
| agataagaag atagtgctgg ctagcctggg ctacatagtg aaacctattt ataaaaccaa | 2340 |
| atcaaaccaa accaaaccaa accaaaccaa accaacaaca caacaacaa caacaaaccc | 2400 |
| cccccccaa aaaaaaccca aaaaccaaaa aaccaaccaa ccaaccgaac aacaacaaaa | 2460 |
| tccagtcaac tcacaatttt cacttaagtg ttatactggc taagtgccat atgtctgacc | 2520 |
| taatggtctt tgccttaaac aattagctgt gtacacagag ggatttcttc catgaagtct | 2580 |
| gaggcagggc atcctgtcct ctgaggattt tcttgatcta ctctaatcct cttttcctgc | 2640 |
| taagatgaat gaatgtagac atctgcggag tcagtgagac aaccgcacga tgattgtttc | 2700 |
| agagcctacg ctgtttccag tctttgtcat tgagtacaca cacggtgcag gtgccctgcg | 2760 |
| cacacactgc ctggttgcta acatcttcta aaggcattgg aaatggatgg gaggcactgg | 2820 |
| tgggtttcat ttccttttcgt gcttgtcctc aactctctga aaagtgtttg gctcagcaga | 2880 |
| ggtgtcccaa ggatgcatgg cttaattgtt cttatagcct ttgctgctac cagtctgcct | 2940 |
| ctgcctccca gtacagggaa gagagtggga agattgagga cacgggagtc aatcagtgtc | 3000 |
| cttccttcca cgtaccagtg gatgaatgga caatttgagt aagacacatc agttaaatgt | 3060 |

```
aatcacagtg tacggctgca acgaaagcaa cttctaattc tgaaagccac agccaacagg    3120
aagccagttc ttctcaaagg ggcaatagct ctcatcaaaa gacattttca tttgtaaaac    3180
tataaagttg tttggaaaat gcggacagga tttattggtc atgtggaacc gaagtgccct    3240
gatgttcact gtgctgcgcc gagccctgcg aaagagcatt tgtaggtaat gcttcataat    3300
gaagttgttc tgcagcccag agaaagaaag aacttactct gaaggtcttc cacatcctct    3360
acccttcacg atccatatat gaatccatct cgatccggac aacagggttt tgtgaaaaac    3420
aaattacgag cactttgtcc ccttttgttc atgttggtaa ggtttcttaa ttgtgttccc    3480
aaacacagag gaccacagcc ttcccctcca agggctgtaa agaatcgtgt gcactttgaa    3540
attgttagag ggaatgcact aagaatattg atggggaggg cactggtttg agcgttttc    3600 aagaaattct cactctttgc ttgagaaggc aaaggcagag agaaatacat tggatgggca    3660
aatagatgca tcagcctgtt gacgacagcc tctgtgtttt aatgctcggc tcaaggcaat    3720
ttctgctacc cccttctctg tctctgccag tggaactatc tcttaaatca agaacaaaat    3780
ttataggagt atcatttgaa aacacttaca ttggagccac cttagttgtt tttaaaaaat    3840
actcatttct agatgtcatc tagacttaac aagatagaat gaaggcctat gtatctgaac    3900
cttccatcaa gagtctagag acaggtaggt agcatgtggt aagaaatgac cactaacttt    3960
taacatcatt gaatttatct tgaagacata gtcattcagg attccttact gttctcagtg    4020
ctaggcatgt ggtgagctaa atggagccat tgatggctca aacagtaatt atactggctt    4080
tcctggcttt ctaacgcctg ctttgggttt aagtataact attaatactg gttcttcgca    4140
cccccaccag caatatttat ttgctgtgca ttgctttact gtactttgtc gaaggtgaat    4200
gagtactttg taagcactct tcaatataca ggcccacccc atttctctgt tgatacacag    4260
tacctggcct caaaatgtct cccaacgagt ccacaaatag ttgagcgaga gtctcaatta    4320
cctctccgcg caggtaatta ttacttctgc catttaagtg aaatttcagt acattgctta    4380
tagaaacaca tttaggagca tatttctgcg gtacctgctt ctattcacag ggtagatttt    4440
aaagttccat ttgtgtcatg ggagagagcg ctaaactgtc cttttgcatg aatttggctg    4500
atagtatatg aaatgttaag atgagctcat tttctccctc tacttctgta agagacttaa    4560
aaaagccaag ccaacaaaca aacctcttcc ctagcaccca atttgcctgc cgtagggagg    4620
gttctatgtc tgtggtcgac tagtaactga gaagttc                             4657
```

<210> SEQ ID NO 2
<211> LENGTH: 2000
<212> TYPE: DNA
<213> ORGANISM: Mus musculus

<400> SEQUENCE: 2

```
ttctatgtct gtggtcgact agtaactgag aagttctgtg gctgctcgct gagctaggaa      60
gtttgccgcc ttgcaccctt ggaagcctct ttatggtctt gaatgagttc tgtgatatgt     120
tttgcagcat gctctttccg acaaggcgtg tgtgaaatcc tttgacccaa agacgacctg     180
cttgcaggaa tgcctaatca ccaccttttca ggacgcttac tttgtttcgg acagttttga    240
agaagccaaa gaaagatga gtaaacctgc ttttcttcct tctatagaaa gtcacttttta     300 aatgtctctc gctgttcctt ctgtctaact gttttttgta cccgtggcgg ttgattgtgt     360
tttccttttg tttttttttt gtttattcta cagggacttt gcaaagtcaa ttacccatcc     420
cttctcggta tacttcaacc cctacacgca gagcattgaa attctgaaag acaccagaag     480
tattgagaat gtggtgcagg acctgcgcag tgatttgaac acagtgtgtg atgccttgaa     540
```

```
taaaatgaac caatatctgg ggatttgagc ctagaaccag agttattgtc agcatgagct    600 cttgggggt gtagcaacaa tgcagtcaat gttatccaac atcaacaact ttctgtgtca     660
tggttggcta gtaagcatgc aattctgtat gtccatacct ctgtgtaact aataacaca    720 aaaatgctct aaagaaccca tgcagataac cactcaccat ttgaaagatt gtgatcctat    780
ttggacatct caagtagagt tgacatttct gattagcgaa caaactgtta acttaagcaa    840
actgtgactt tgaaatctgt agcaaacatt cctcgcacaa ttccagtcgg tgagttgtgg    900
aacttttctt ccttggacct gagactttcc tctgtgttca ttagataaaa tgaaaatagt    960
tgggaggtgg tttctatttt caatagtatc cgtgttattt gagataaact agagttgctc   1020
cacgctttgc atcacagcaa caaaggattt aatattctac ttcagaagct gttcagaaac   1080
acagcagttg ggatggatgt agactgagtg ttcagacaat gcaagcaaag aaaagttttg   1140
ataaacagga tatataggtt gtactgacct cgttgaaacc aatttgtggc aagcttcctg   1200
aagagcttct ggaaggaaac acttgaacaa agaatattcg ggaagcttaa acagaaggga   1260
tgaaaatctt ggaactgtga atgtattgtt aggatagagt gaattatcac tgcaggcttt   1320
tgactccttt tgcttagact gagaacctca aatcccacag ggatgtaaat accatctctg   1380
attccaaaga gttggagacg gagtcgtaga gaaacaaagg gatttgcttc agttaggtct   1440
gatgagatgt gccatggtca taagccactg ccctttatg ttggacatct gacaagtcta   1500
ctgtagtgta catgcatgtt tatgtattga cacagaaaga aaattattgc ttataaaatg   1560
aatgcttctc aataaacaga atcttgcccc caacagggta tctcttatct catctcacac   1620
cttgaaaaca ggctctgtct atggggaggg agattttct caaaatctgg ggcaactctg    1680
ggtaaacaat agtgatttgc tgtaaatgtc tggtgatttt tgctataaaa gataaaaagc   1740
aaacgaacat tctcccctcc cccaaaaat cccaagtgtc taagtgagca agtgaaaaac    1800
tgctgaatca gttaatttaa ttatcttcaa atgggttccc tcatcgaaca agcctcctaa   1860
ttctgctcct tttgggaagc agtgcagggg ctggacagag tgggaggggt aggggcgaga   1920
ggtatagaag gagacagaaa aaaaactttt aagttagagt attggctagt tttctattcc   1980
tgtgataaaa caccatgacc                                              2000
```

```
<210> SEQ ID NO 3
<211> LENGTH: 20
<212> TYPE: DNA
<213> ORGANISM: Artificial
<220> FEATURE:
<223> OTHER INFORMATION: PCR primer

<400> SEQUENCE: 3
cacccaattt gccgtaggga                                                 20

<210> SEQ ID NO 4
<211> LENGTH: 35
<212> TYPE: DNA
<213> ORGANISM: Artificial
<220> FEATURE:
<223> OTHER INFORMATION: PCR primer

<400> SEQUENCE: 4
gctgcaaaac atatcacaga actcattcaa gacca                                35

<210> SEQ ID NO 5
<211> LENGTH: 33
<212> TYPE: DNA
<213> ORGANISM: Artificial
<220> FEATURE:
```

```
<223> OTHER INFORMATION: PCR primer

<400> SEQUENCE: 5
tggtcttgaa tgagttctgt gatatgtttt gca                              33

<210> SEQ ID NO 6
<211> LENGTH: 29
<212> TYPE: DNA
<213> ORGANISM: Artificial
<220> FEATURE:
<223> OTHER INFORMATION: PCR primer

<400> SEQUENCE: 6
tcatgctgac aataactctg gttctaggc                                   29

<210> SEQ ID NO 7
<211> LENGTH: 28
<212> TYPE: DNA
<213> ORGANISM: Artificial
<220> FEATURE:
<223> OTHER INFORMATION: PCR primer

<400> SEQUENCE: 7
taggggttga agtataccga gaaggcac                                    28

<210> SEQ ID NO 8
<211> LENGTH: 28
<212> TYPE: DNA
<213> ORGANISM: Artificial
<220> FEATURE:
<223> OTHER INFORMATION: PCR primer

<400> SEQUENCE: 8
taggggttga agtataccga gaaggcat                                    28
```